United States Patent
Grinberg et al.

(10) Patent No.: US 8,298,235 B2
(45) Date of Patent: Oct. 30, 2012

(54) INSTRUMENT AND METHOD FOR THE INSERTION AND ALIGNMENT OF AN INTERVERTEBRAL IMPLANT

(75) Inventors: Alexander Grinberg, Newton, MA (US); William McGittigan, Bourne, MA (US); Edward B. Zalenski, Lakeville, MA (US); Ronald Garner, Hull, MA (US); Andrea Burke, Hudson, MA (US)

(73) Assignee: DePuy Spine, Inc., Raynham, MA (US)

( * ) Notice: Subject to any disclaimer, the term of this patent is extended or adjusted under 35 U.S.C. 154(b) by 1541 days.

(21) Appl. No.: 11/026,342

(22) Filed: Dec. 30, 2004

(65) Prior Publication Data

US 2006/0084986 A1   Apr. 20, 2006

Related U.S. Application Data

(60) Provisional application No. 60/615,544, filed on Sep. 30, 2004.

(51) Int. Cl.
*A61F 2/30* (2006.01)

(52) U.S. Cl. ..................................... 606/86 A

(58) Field of Classification Search .............. 606/60–63, 606/86 A, 96, 99; 623/17.11–17.16
See application file for complete search history.

(56) References Cited

U.S. PATENT DOCUMENTS

| | | | |
|---|---|---|---|
| 5,431,658 A | | 7/1995 | Moskovich |
| 5,486,187 A | * | 1/1996 | Schenck ........................ 606/153 |
| 5,505,732 A | | 4/1996 | Michelson |
| 5,722,977 A | * | 3/1998 | Wilhelmy ........................ 606/84 |
| 5,782,830 A | * | 7/1998 | Farris ............................... 606/99 |
| 6,113,637 A | * | 9/2000 | Gill et al. ...................... 623/17.15 |
| 6,241,729 B1 | * | 6/2001 | Estes et al. ................... 606/86 R |
| 6,371,986 B1 | | 4/2002 | Bagby |
| 6,440,139 B2 | * | 8/2002 | Michelson ....................... 606/80 |

(Continued)

FOREIGN PATENT DOCUMENTS

EP   0 535 973 B1   7/1993

(Continued)

OTHER PUBLICATIONS

Krag, M.H., et al., "An Internal Fixator for Posterior Application to Short Segments of the Thoracic, Lumbar or Lumbosacral Spine," *Clinical Orthopaedics and Related Research*, 203, pp. 75-98, Feb. 1986.

*Primary Examiner* — Kevin T Truong
*Assistant Examiner* — Christopher Beccia
(74) *Attorney, Agent, or Firm* — Nutter McClennen & Fish LLP

(57) ABSTRACT

The present invention includes pin guides and methods for placing pins in adjacent vertebrae. The present invention also includes methods for placing pins in adjacent vertebrae using the pin guides described herein. The present invention also includes an intervertebral implant insertion and alignment instrument, a distraction instrument, an intervertebral implant insertion guide, and methods for inserting an implant into an intervertebral space. Despite existing tools and techniques, present positioning of implants in intervertebral spaces and pins in adjacent vertebrae often depend on a surgeon's skill, experience and technique. Practice of the present invention can aide in the placement of an implant into an intervertebral space and placement of pins in adjacent vertebrae, e.g., midline to the coronal plane spine and/or parallel to vertebral endplates that abut the intervertebral space.

23 Claims, 31 Drawing Sheets

U.S. PATENT DOCUMENTS

| | | |
|---|---|---|
| 6,517,544 B1 | 2/2003 | Michelson |
| 6,524,312 B2 * | 2/2003 | Landry et al. ............... 606/86 A |
| 6,599,292 B1 | 7/2003 | Ray |
| 6,599,294 B2 | 7/2003 | Fuss et al. |
| 6,648,891 B2 | 11/2003 | Kim |
| 6,692,501 B2 | 2/2004 | Michelson |
| 6,712,818 B1 | 3/2004 | Michelson |
| 7,479,160 B2 * | 1/2009 | Branch et al. ............. 623/17.11 |
| 7,527,629 B2 * | 5/2009 | Link et al. ..................... 606/87 |
| 7,753,911 B2 * | 7/2010 | Ray et al. ................... 606/86 A |
| 7,794,465 B2 * | 9/2010 | Marik et al. ................... 606/87 |
| 7,832,409 B2 * | 11/2010 | Richelsoph et al. .......... 128/898 |
| 2002/0116009 A1 | 8/2002 | Fraser et al. |
| 2002/0161366 A1 * | 10/2002 | Robie et al. ..................... 606/61 |
| 2003/0060687 A1 * | 3/2003 | Kleeman et al. ............. 600/235 |
| 2003/0135275 A1 * | 7/2003 | Garcia et al. ............... 623/17.11 |
| 2003/0135277 A1 * | 7/2003 | Bryan et al. ............... 623/17.12 |
| 2003/0171813 A1 * | 9/2003 | Kiester ....................... 623/17.11 |
| 2003/0199872 A1 | 10/2003 | Markworth et al. |
| 2003/0216744 A1 | 11/2003 | Longhini et al. |
| 2003/0236526 A1 * | 12/2003 | Van Hoeck et al. ............. 606/90 |
| 2004/0002712 A1 * | 1/2004 | Grinberg et al. ................ 606/79 |
| 2004/0010259 A1 * | 1/2004 | Keller et al. ..................... 606/80 |
| 2004/0078079 A1 * | 4/2004 | Foley .......................... 623/17.11 |
| 2004/0162563 A1 * | 8/2004 | Michelson ....................... 606/79 |
| 2007/0123985 A1 * | 5/2007 | Errico et al. ................ 623/17.11 |

FOREIGN PATENT DOCUMENTS

| | | |
|---|---|---|
| EP | 0 630 615 A1 | 12/1994 |
| EP | 1 344 493 A1 | 9/2003 |
| FR | 2 636 227 | 3/1990 |
| FR | 2 717 068 | 9/1995 |
| WO | WO 97/38634 | 10/1997 |

* cited by examiner

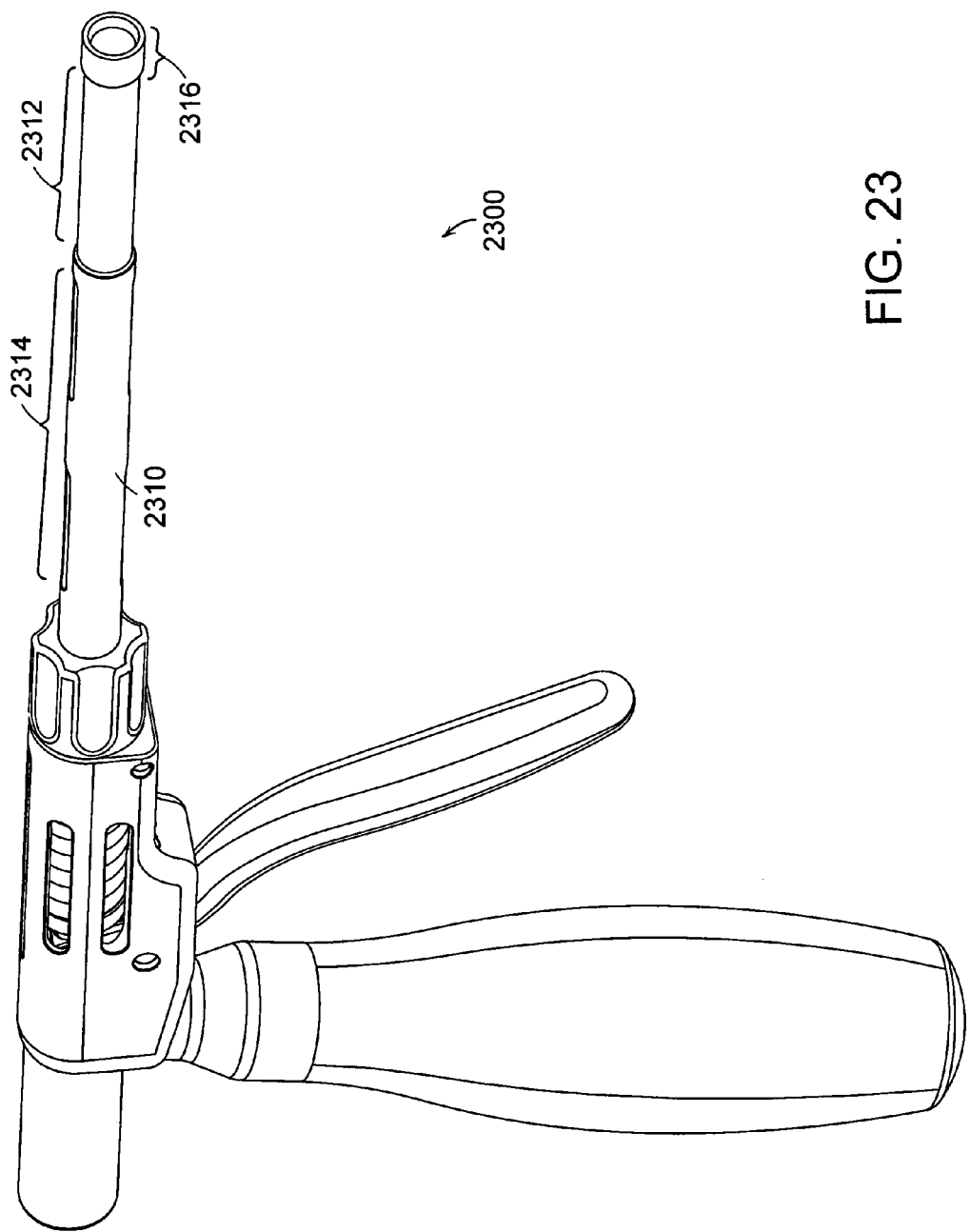

INSTRUMENT AND METHOD FOR THE INSERTION AND ALIGNMENT OF AN INTERVERTEBRAL IMPLANT

RELATED APPLICATION

This application claims the benefit of U.S. Provisional Application No. 60/615,544, filed Sep. 30, 2004, the entire teachings of which are incorporated herein by reference.

BACKGROUND OF THE INVENTION

Spinal surgery involves many challenges as the long-term health and mobility of the patient often depends on the surgeon's technique and precision. One type of spinal surgery involves the removal of an existing intervertebral disc located between adjacent vertebral bodies. Procedures are known in which an existing intervertebral disc, for example, natural damaged disc tissue, is replaced with a disc prosthesis or with an interbody cage or fusion device. Replacement of a vertebral disc can include removing an existing intervertebral disc or portion of an intervertebral disc, distracting apart vertebral bodies, and inserting a replacement intervertebral disc into the intervertebral space.

This process can present the surgeon with several challenges. For example, the adjacent vertebral bodies typically collapse upon each other once the existing disc is removed. These vertebral bodies must be separated to an extent sufficient to enable the placement of the replacement intervertebral disc. However, if the vertebral bodies are separated, or distracted, beyond a certain degree, injury to the patient can occur.

There are several tools and techniques known for distracting apart vertebral bodies. One technique includes anchoring a pin in each of two adjacent vertebrae and imparting a force to the pins to distract the adjacent vertebrae. Typically, a pin is anchored into a vertebra by a surgeon who places the pin by hand based on landmark features of the vertebra bone and using heuristics gained from experience. In some instances, the surgeon can use fluoroscopy or x-ray to verify the position of the pin after the pin is anchored in the vertebra. Then, if necessary, the pin can be removed from the vertebra and the pin repositioned. Because the pins are typically positioned by hand and the final position and alignment of the pins can depend on the surgeon's skill, experience and technique, the pins are generally not consistently positioned nor typically is the alignment of a pin consistent with the alignment of the pin in the adjacent vertebra. In some instances, the procedure may include trial and error to gain a desired pin position and alignment.

There are also several tools and techniques known for inserting and aligning an intervertebral implant such as a prosthetic disc in an intervertebral space. Proper insertion and alignment of an intervertebral implant can be of great importance, but unfortunately, this process can be challenging interoperatively and the specific placement of implants can vary from one surgeon to the next.

A need exists for tools and methods for placing pins in vertebrae and for inserting and aligning intervertebral implants between vertebrae that overcome or minimize the above-referenced problems.

SUMMARY OF THE INVENTION

The present invention includes pin guides and methods for placing pins in adjacent vertebrae. Despite existing tools and techniques, present placement of pins in vertebrae often depends on a surgeon's skill, experience and technique. Practice of the present invention can aide in the placement of pins, e.g., midline to the spine. Practice of the present invention is suitable for, for example, the placement of pins in vertebrae typically used in spinal fusion surgery and disc replacement surgery. In one embodiment, the present invention can be used to place distraction pins in adjacent vertebrae for subsequent distraction using a suitable distraction apparatus.

In one embodiment, the pin guide is modular and includes a spacer component and a guide component. The spacer component can include an intervertebral spacer and a coupling member. The guide component can define a plurality of parallel guide tubes, e.g., holes, extending from a first side of the guide component to a second side of the guide component and bracketing a central hole defined by the guide component, wherein the central hole is adapted to receive the coupling member.

The present invention also includes a method for placing pins in adjacent vertebrae that includes positioning between adjacent vertebrae an intervertebral spacer of a spacer component that includes the intervertebral spacer and a coupling member; positioning a guide component defining a plurality of parallel guide tubes, e.g., holes, extending from a first side of the guide component to a second side of the guide component and bracketing a central hole defined by the guide component, wherein the central hole is adapted to receive the coupling member, onto the coupling member of the spacer component; and placing pins in the adjacent vertebrae through at least two of the plurality of parallel guide tubes.

In one embodiment, the invention includes a pin guide comprising a support; an intervertebral spacer projecting from the support; and a plurality of parallel guide tubes e.g., holes, extending through the support, wherein the parallel guide tubes are sized to align pins inserted into the guide tubes in a substantially parallel orientation. An additional method for placing pins in adjacent vertebrae is also described herein. In that method, the intervertebral spacer of the pin guide is positioned between adjacent vertebrae; and pins are placed in the adjacent vertebrae through at least two of the plurality of parallel guide tubes.

By practicing the present invention, pins can be placed midline (lateral/medial) to the spine of a patient. Furthermore, midline placement of the pins in adjacent vertebrae using the present invention can be more reliable and reproducible than present methods for placing pins in adjacent vertebrae. Practice of the present invention also provides reliably correct alignment of pins in adjacent vertebrae. For example, practice of the invention can provide substantial parallel alignment of pins placed in adjacent vertebrae. The present invention can also produce parallel alignment of pins with the endplates of the vertebrae in which the pins are placed.

Through practice of the present invention, correctly aligned pins can be placed into vertebrae using the pin guide using the relatively easy and reliable methods described herein. Practice of the present invention can also provide anterior/posterior sizing information and superior/inferior sizing information for an intervertebral implant subsequently inserted into the intervertebral space.

The present invention also includes instruments and methods for inserting and aligning intervertebral implants within an intervertebral space. In one aspect, an intervertebral implant insertion and alignment instrument is described. A distraction instrument and an intervertebral implant insertion guide are also described herein. Methods for inserting an intervertebral implant, e.g., a prosthetic disc or a graft, into an intervertebral space are also described. In some embodiments, the herein-described pin guides and methods for placing pins in adjacent vertebrae are used in conjunction with the instruments and methods for inserting and aligning intervertebral implants within an intervertebral space.

The present invention includes an intervertebral implant insertion and alignment instrument that includes a rotatable bearing fixture defining an opening for receiving a shaft of a distraction instrument; and a cannular instrument guide coupled to the rotatable bearing fixture. In one embodiment, the intervertebral prosthetic implant insertion and alignment instrument is adapted for use in conjunction with a vertebral distractor. For example, the rotatable bearing fixture can define an opening for receiving a shaft of a vertebral distractor.

The present invention also includes a method for inserting an implant into an intervertebral space. The method includes placing distraction pins into adjacent vertebrae which abut the intervertebral space; placing a distraction instrument onto the distraction pins, wherein the distraction instrument includes a cannular instrument guide; placing an implant insertion instrument into the cannular instrument guide; and inserting the implant into the intervertebral space using the implant insertion instrument, wherein the implant insertion instrument is guided by the cannular instrument guide.

In one embodiment, the invention includes a distraction instrument that includes a pair of first and second opposed distraction arms; wherein the distraction arms each define a cannular pin sleeve sized to fit onto distraction pins anchored in vertebral bone such that a portion of each distraction pin distal to the vertebral bone is exposed after the cannular pin sleeves are placed on the distraction pins; and a distraction force transmitting member coupled to the distraction arms.

The present invention also includes an intervertebral implant insertion guide. The intervertebral implant insertion guide includes a cannular guide body, defining a cannular space shaped to receive an intervertebral implant insertion instrument, and two cannular pin sleeves sized to fit onto distraction pins anchored in vertebral bone, wherein the cannular pin sleeves are coupled to the cannular guide body. In one embodiment, the distraction instrument and the intervertebral implant insertion guide constitute a system for inserting and aligning an implant in an intervertebral space.

In one aspect, the present invention includes another method for inserting an implant into an intervertebral space. This method can include placing distraction pins into adjacent vertebrae which abut the intervertebral space; placing a distraction instrument onto the distraction pins, such that a portion of each distraction pin distal to the vertebral bone remains exposed after placement of the distraction instrument onto the distraction pins; placing an intervertebral implant insertion guide onto the portions of the distraction pins that remained exposed after placement of the distraction instrument onto the distraction pins; and inserting the implant into the intervertebral space using an implant insertion instrument, wherein the implant insertion instrument is guided by the intervertebral implant insertion guide.

Despite existing tools and techniques, present insertion and alignment of an intervertebral implant within an intervertebral space, like the placement of pins, described supra, often depends on a surgeon's skill, experience and technique. Practice of the present invention can aide in the insertion and alignment of intervertebral implants within an intervertebral space, e.g., midline to the coronal plane of the spine and parallel to the endplates of the vertebrae that abut the intervertebral space. Practice of the present invention is suitable for, for example, the insertion and alignment of implants typically used in disc replacement surgery or in spinal fusion surgery. By practicing the present invention, a surgeon can properly position an implant into an intervertebral space. Among other advantages, proper positioning of an intervertebral implant can reduce stresses on the facets, can reduce the likelihood of implant expulsion, can provide proper kinematics for the implant and spine, and can reduce wear of the implant. Furthermore, the methods and instruments described herein can be used to consistently position an implant within the intervertebral space.

BRIEF DESCRIPTION OF THE DRAWINGS

FIG. 23 shows an implant inserter suitable for use with the present invention.

DETAILED DESCRIPTION OF THE INVENTION

Figure 1:
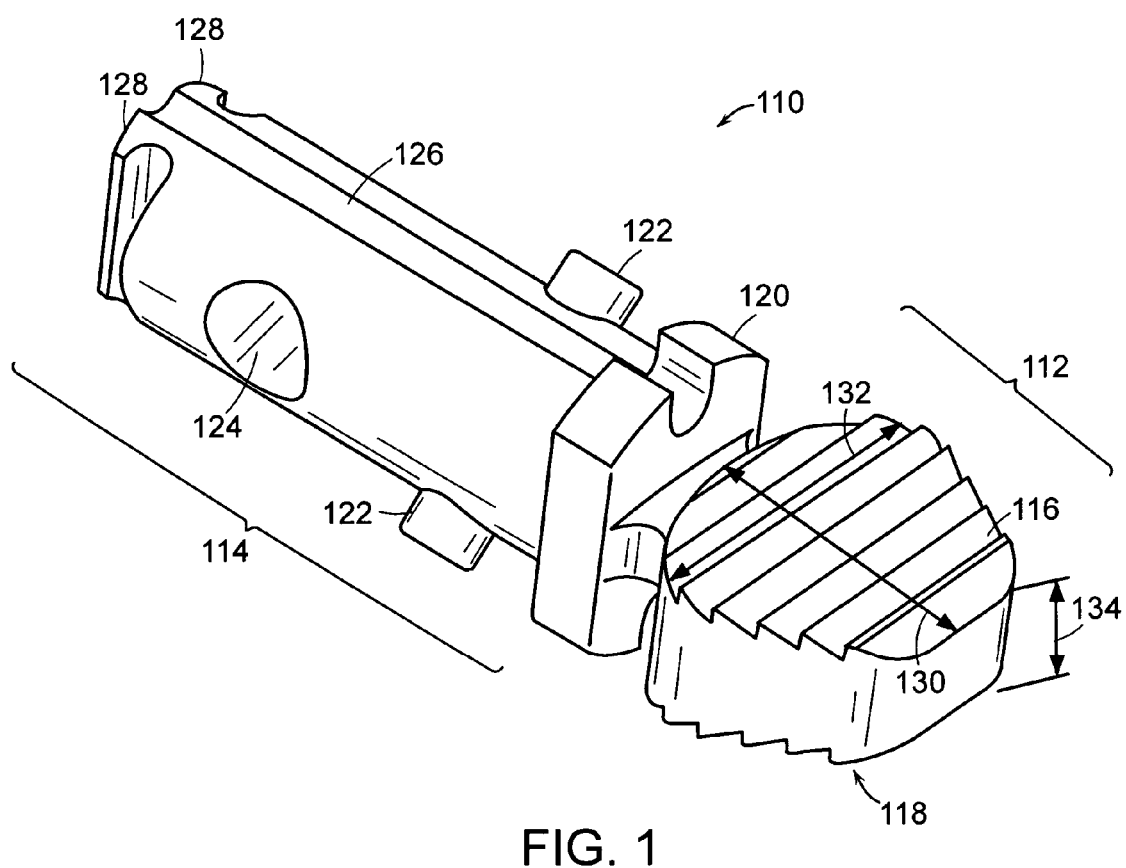
FIG. 1 is a perspective view of a spacer component of a modular pin guide according to one embodiment of the present invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The present invention includes pin guides and methods for placing pins in adjacent vertebrae. The term "pin," as used herein, refers to a pin (e.g., a threaded or partially threaded pin) or screw suitable for use in spine surgical procedures. For example, pins suitable for use with the present invention include distraction pins.

The present invention includes a modular pin guide comprising (a) a spacer component including an intervertebral spacer and a coupling member; and (b) a guide component defining a plurality of parallel guide tubes extending from a first side of the guide component to a second side of the guide component and bracketing a central hole defined by the guide component, wherein the central hole is adapted to receive the coupling member.

FIG. 1 illustrates spacer component 110 according to one embodiment of the present invention. Spacer component 110 can be constructed of any material compatible with surgical procedures, for example, any material capable of sterilization and capable of withstanding stresses applied during use of the component in surgery. In one preferred embodiment, spacer component 110 is constructed of a substantially radiopaque material such as, for example, radiopaque ceramic, stainless steel, titanium, tantalum cobalt, chromium, aluminum, and combinations thereof. In another embodiment, spacer component 110 is constructed of a substantially radiolucent material such as a substantially radiolucent plastic. In another embodiment, spacer component 110 is a composite of radiopaque and radiolucent materials.

Spacer component 110 includes intervertebral spacer 112. Intervertebral spacer 112 includes first surface 116 and second surface 118. FIG. 1 illustrates first surface 116 and second surface 118 having ridges or teeth thereon. In some embodiments, at least first surface 116 or second surface 118 includes a textured surface, e.g., a ridged or toothed surface. The textured surface can include a patterned textured surface or the textured surface can have irregular texturing. First surface 116 and second surface 118 are preferably adapted for contact with adjacent vertebral bodies. As illustrated in FIG. 1, first surface 116 and second surface 118 of intervertebral spacer 112 skew toward one another, e.g., first surface 116 and second surface 118 form a lordotic angle. In other embodiments not illustrated in FIG. 1, first surface 116 and second surface 118 are parallel or substantially parallel.

Spacer component 110 also includes coupling member 114. Coupling member 114 can be cylindrical, as illustrated in FIG. 1. In other embodiments, coupling member 114 is a non-circular column. For example, the coupling member can be a rectangular, square, triangular, cross-shaped, star-shaped or irregularly-shaped column. Coupling member 114 is shaped and sized to fit the central hole defined by the guide component, described infra.

Spacer component 110 can also include vertebral stop 120. Vertebral stop 120 can be used to prevent over-insertion of intervertebral spacer 112 into an intervertebral space. Vertebral stop 120 can abut vertebral bone when intervertebral spacer 112 is inserted into the intervertebral space to a desired depth.

FIG. 1 illustrates anti-rotation element 122 as a peg element. In another embodiment, the anti-rotation element is a slot for receiving a corresponding anti-rotation element present in the central hole of the guide component, described infra. In a preferred embodiment, if coupling member 114 includes a cylindrical member, then the coupling member also includes at least one anti-rotation element. Preferably, anti-rotation element 122 is adapted to fit the central hole defined by the guide component, described infra.

Coupling member 114 also can include orientation markers such as marker hole 124 and marker groove 126. In one embodiment, the orientation marker is a cylindrical marker hole such as marker hole 124. In one embodiment, at least a portion of the coupling member surrounding the orientation marker is radiopaque. For example, the portion of the coupling member surrounding marker hole 124 is radiopaque.

As illustrated in FIG. 1, an orientation marker, marker hole 124, is defined by coupling member 114. Marker groove 126 is shown extending along the superior ridge of coupling member 114 and also through vertebral stop 120. Another marker groove can also extend along the inferior ridge of coupling member 114 and also through vertebral stop 120, the illustration of which is partially obscured in the view of FIG. 1. The orientation marker can be of any size or shape whereby orientation of the spacer component can be determined when fluoroscopy, x-ray, or eyesight is used to assess position of the spacer component.

Spacer component 110 illustrated in FIG. 1 also includes instrument handle 128. Instrument handle 128 is on coupling member 110 and is located distally to intervertebral spacer 112. In one embodiment, instrument handle 128 is adapted to be received by a general purpose surgical instrument. For example, instrument handle 128 can be adapted to be received by the same grabber instrument that is used to position the guide component, described infra. In one embodiment, instrument handle 128 is a projection, for example, a projection molded or machined into coupling member 114. In one embodiment, instrument handle 128 is a dovetailed projection as illustrated in FIG. 1.

Intervertebral spacer 112, described supra, can be supplied in a variety of dimensions depending on the particular surgical application. Intervertebral spacer 112 has depth 130, width 132, and height 134. In some embodiments, depth 130 ranges from about 12 to about 16 millimeters (mm), width 132 ranges from about 14.5 to about 19 mm, and height 134 ranges from about 5 to about 10 mm. For example, intervertebral spacer 112 can have a footprint of about 12 mm by about 14.5 mm, about 14 by about 17 mm, or about 16 mm by about 19 mm (depth 132 by width 130). Intervertebral spacer 112 can have height 134 of, for example, about 5, 6, 7, 8, 9, or about 10 mm.

Figure 2:
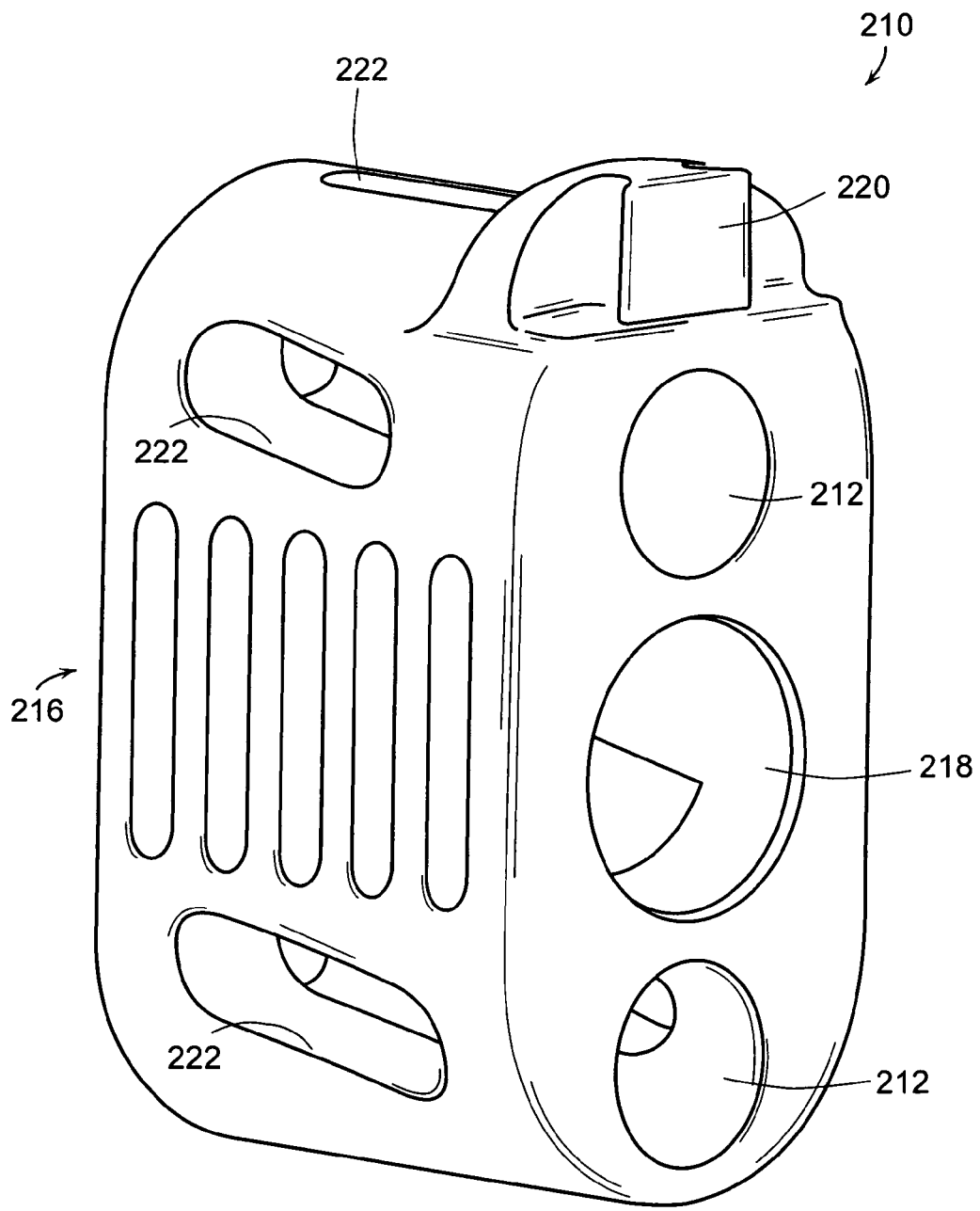
FIG. 2 is a perspective view of a guide component of a modular pin guide according to one embodiment of the present invention.

FIG. 2 illustrates guide component 210 according to one embodiment of the present invention. Guide component 210 defines a plurality of parallel guide tubes 212 e.g., holes, extending from a first side 214 of the guide component to a second side 216 of the guide component. In a preferred embodiment, guide component 210 defines two parallel guide tubes. Preferably, the parallel guide tubes are of sufficient length and of sufficient diameter to maintain an inserted pin in alignment with the guide tube as the pin is placed into a vertebra. In one embodiment, the parallel guide tubes are of sufficient diameter to maintain an inserted surgical instrument in alignment with the guide tube, for example, the parallel guide tubes are of sufficient diameter to maintain an inserted driver in alignment with the guide tube. In one embodiment, each of the parallel guide tubes 212 has a length greater than its diameter. In one embodiment, each of the parallel guide tubes 212 has a length at least equal to the thread engagement length of the pin to be inserted therein. In one embodiment, each of parallel guide tubes 212 has a length of at least about 12 mm such as a length in the range of from at least about 12 mm to at least about 16 mm.

Guide component 210 also defines central hole 218 adapted to receive coupling member 114 of the spacer component. Parallel guide tubes 212 bracket central hole 218. For example, at least one parallel guide tube is located superior to central hole 218 and at least one parallel guide tube is located inferior to central hole 218. Central hole 218 can extend from first side 214 of the guide component to second side 216 of the guide component, as illustrated in FIG. 2. In another embodiment, central hole 218 can extend from second side 216 only partially through guide component 210. Generally, central hole 218 is parallel to parallel guide tubes 212. Central hole 218 is adapted to receive coupling member 114 of the spacer component. For example, central hole 218 is sized and shaped so that at least a portion of coupling member 114 fits into central hole 218.

If coupling member 114 includes an anti-rotation element, e.g., anti-rotation element 122, central hole 218 can be shaped and sized to accommodate the anti-rotation element. For example, central hole 218 can include an anti-rotation element, such as a slot, that accommodates a corresponding anti-rotation element on coupling member 114, such as a peg. In another embodiment, central hole 218 contains an anti-rotation element, e.g., a peg (not shown in FIG. 2), that fits an anti-rotation element of coupling member 114, e.g., a slot (not shown in FIG. 2). In one embodiment, central hole 218 contains at least one anti-rotation element.

Guide component 210 also can include orientation markers such as marker holes or marker grooves. In one embodiment, the orientation marker is a cylindrical marker hole defined by guide component 210. For example, the orientation marker can be a marker hole defined by guide component 210 and extending substantially perpendicularly to central hole 218. In one embodiment, at least a portion of guide component 210 surrounding the orientation marker is radiopaque. The orientation marker can be of any size or shape whereby orientation of the guide component can be determined when fluoroscopy, x-ray, or eyesight is used to assess position of the guide component.

Guide component 210 illustrated in FIG. 2 also includes instrument handle 220. In one embodiment, instrument handle 220 is adapted to be received by a general purpose surgical instrument. For example, instrument handle 220 can be adapted to be received by the same grabber instrument that is used to position the spacer component, described supra. In one embodiment, instrument handle 220 is a projection, for example, a projection molded or machined into guide component 210. In one embodiment, instrument handle 210 is a dovetailed projection as illustrated in FIG. 2.

Guide component 210 can also define one or more guide windows 220. Guide window 222 permits viewing of the interior of parallel guide tube 212. As described in detail infra, a surgeon can use guide window 222 to determine the depth of an instrument or screw within the guide component.

In one preferred embodiment, guide component 210 is constructed of a substantially radiolucent material, such as substantially radiolucent plastic. In another embodiment, guide component 210 is constructed of a substantially radiopaque material, such as stainless steel. In another embodiment, guide component 210 is a composite of radiopaque and radiolucent materials.

Also described herein is a method for placing pins in adjacent vertebrae. The method comprises the steps of (a) positioning between adjacent vertebrae an intervertebral spacer of a spacer component that includes the intervertebral spacer and a coupling member; (b) positioning a guide component defining a plurality of parallel guide tubes extending from a first side of the guide component to a second side of the guide component and bracketing a central hole defined by the guide component, wherein the central hole is adapted to receive the coupling member, onto the coupling member of the spacer component; and (c) placing pins in the adjacent vertebrae through at least two of the plurality of parallel guide tubes. Typically, the methods described herein further include the additional step of exposing the spine of a patient through an anterior approach prior to positioning the intervertebral spacer.

Figure 3:
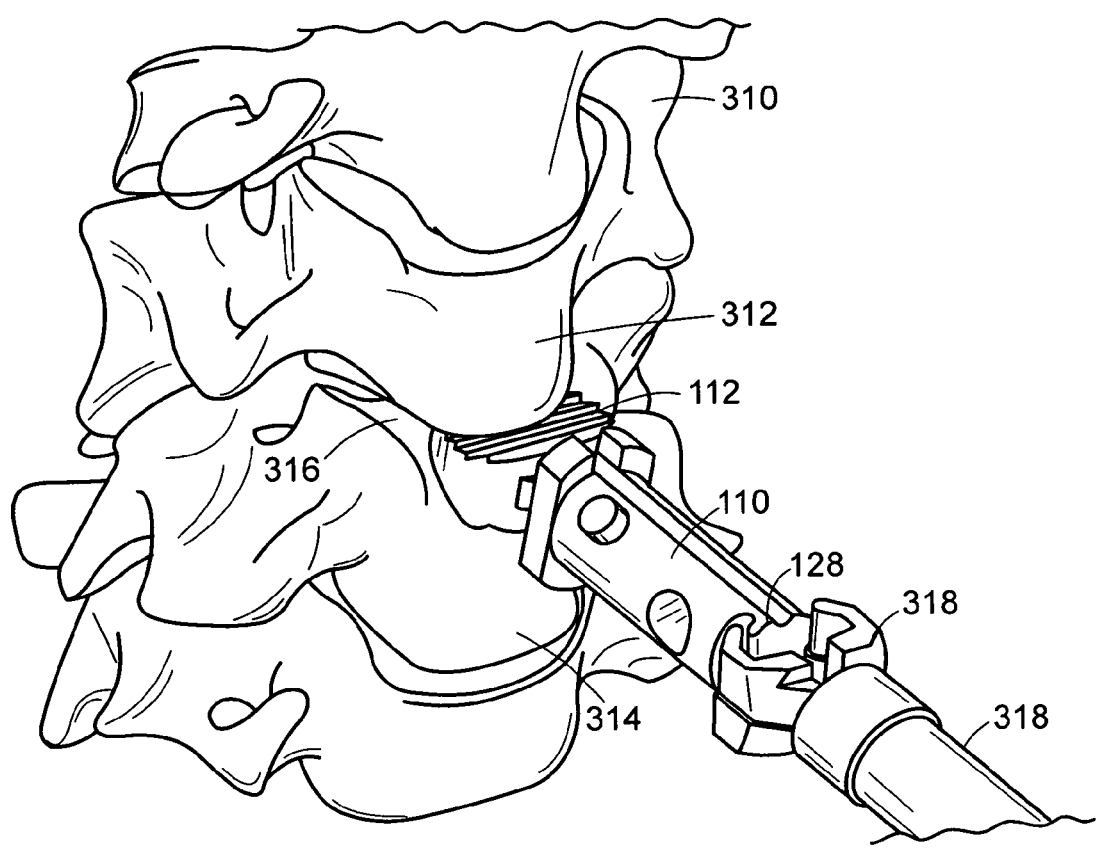
FIG. 3 illustrates insertion of a spacer component of a modular pin guide into an intervertebral space.

FIG. 3 illustrates positioning of spacer component 110 and includes an anterior perspective view of a spinal column. Spinal column 310 includes superior vertebra 312 and inferior vertebra 314 which enclose intervertebral space 316. The method for placing pins in adjacent vertebrae includes the step of positioning intervertebral spacer 112 between adjacent vertebrae. FIG. 3 shows the insertion of intervertebral spacer 112 into intervertebral space 316. Surgical instrument 318 can be used to grasp spacer component 110 at instrument handle 128. Spacer component 110 can be used to determine acceptable anterior/posterior positioning of the intervertebral spacer and suitable dimensions for the intervertebral spacer (e.g., footprint and height).

In one embodiment, spacer component 110 includes a substantially radiopaque orientation marker and the method for placing pins in adjacent vertebrae further includes the step of using fluoroscopy or x-ray and the orientation marker to determine the position of the spacer component after positioning intervertebral spacer 112 between the adjacent vertebrae. For example, in one embodiment, the orientation marker is cylindrical marker hole 124 defined by spacer component 110 and a sagittal image is produced using fluoroscopy or x-ray. Proper orientation of spacer component 110 can be indicated by the appearance of the orientation marker as a circle in the sagittal image.

In one embodiment, the method includes the additional step of removing an intervertebral disc or a portion of an disc from between adjacent vertebrae, e.g., superior vertebra 312 and inferior vertebra 314, prior to positioning intervertebral spacer 112 between those adjacent vertebrae.

Spacer component 110 can be selected from among a group of spacer components each having an intervertebral spacer of a particular dimension. Surgeons can select a spacer component 110 depending on such circumstances as, for example, the location and size of the particular intervertebral space of interest. Examples of suitable sizes for intervertebral spacers are described supra.

Figure 4:
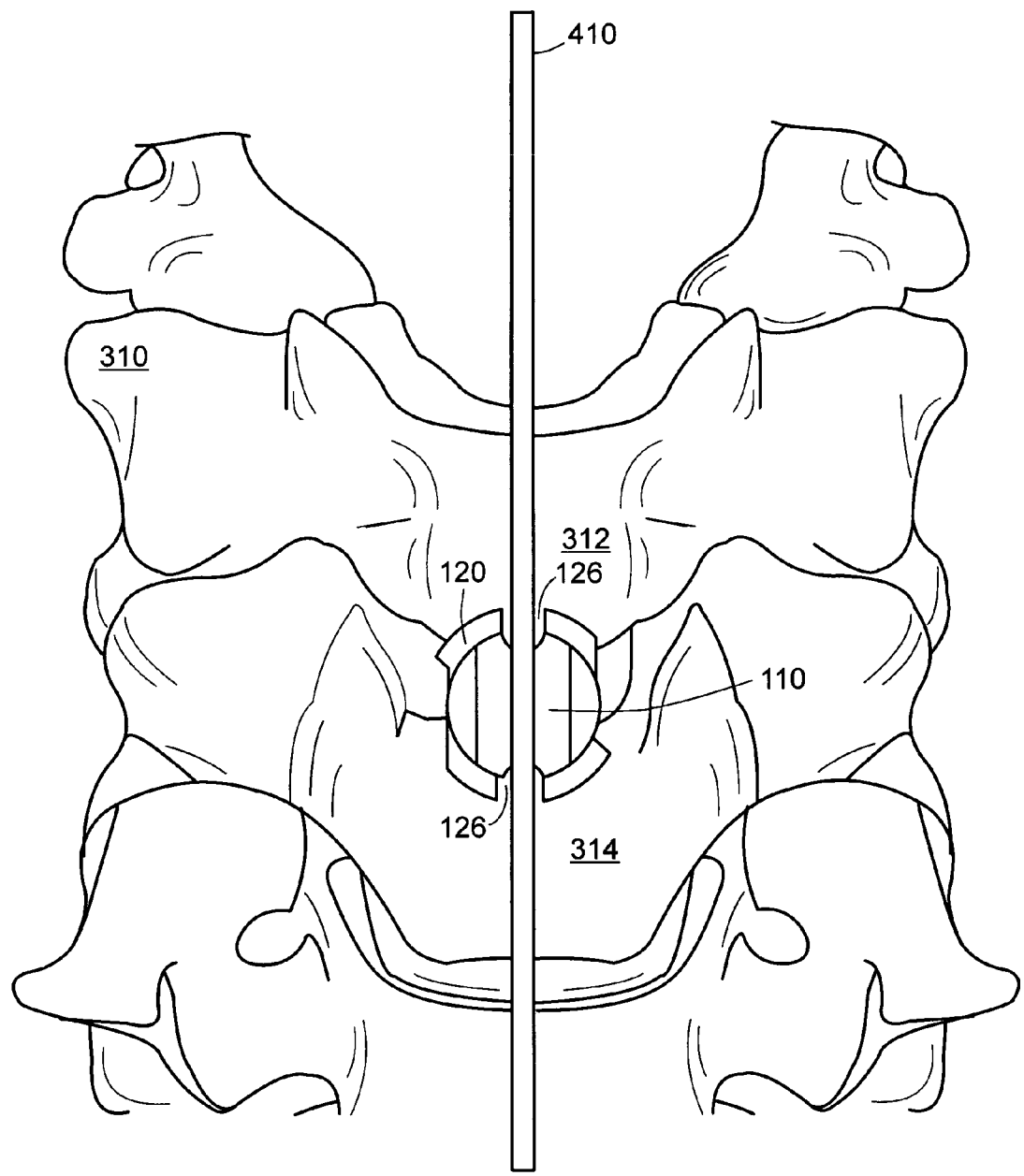
FIG. 4 shows midline alignment of a modular pin guide spacer component inserted into an intervertebral space.

FIG. 4 shows midline alignment (lateral/medial) of a modular pin guide spacer component inserted into an intervertebral space. A surgeon can position the spacer component, for example, with reference to existing anatomical markers such as the spinous process, the pedicle, the uncinate processes and the vertebral body. In one embodiment, the surgeon can use the sides of spacer component 110 or vertebral stop 120 in relation to anatomical markers to position the spacer component. Spacer component 110 with marker groove 126 is shown in FIG. 4 aligned along spine midline 410. A surgeon can use marker groove 126 to help determine alignment of spacer component 110 relative to midline 410. The surgeon can then adjust the positioning of spacer component 110, if necessary. FIG. 4 also illustrates the abutment of vertebral stop 120 against spinal column 310.

Figure 5:
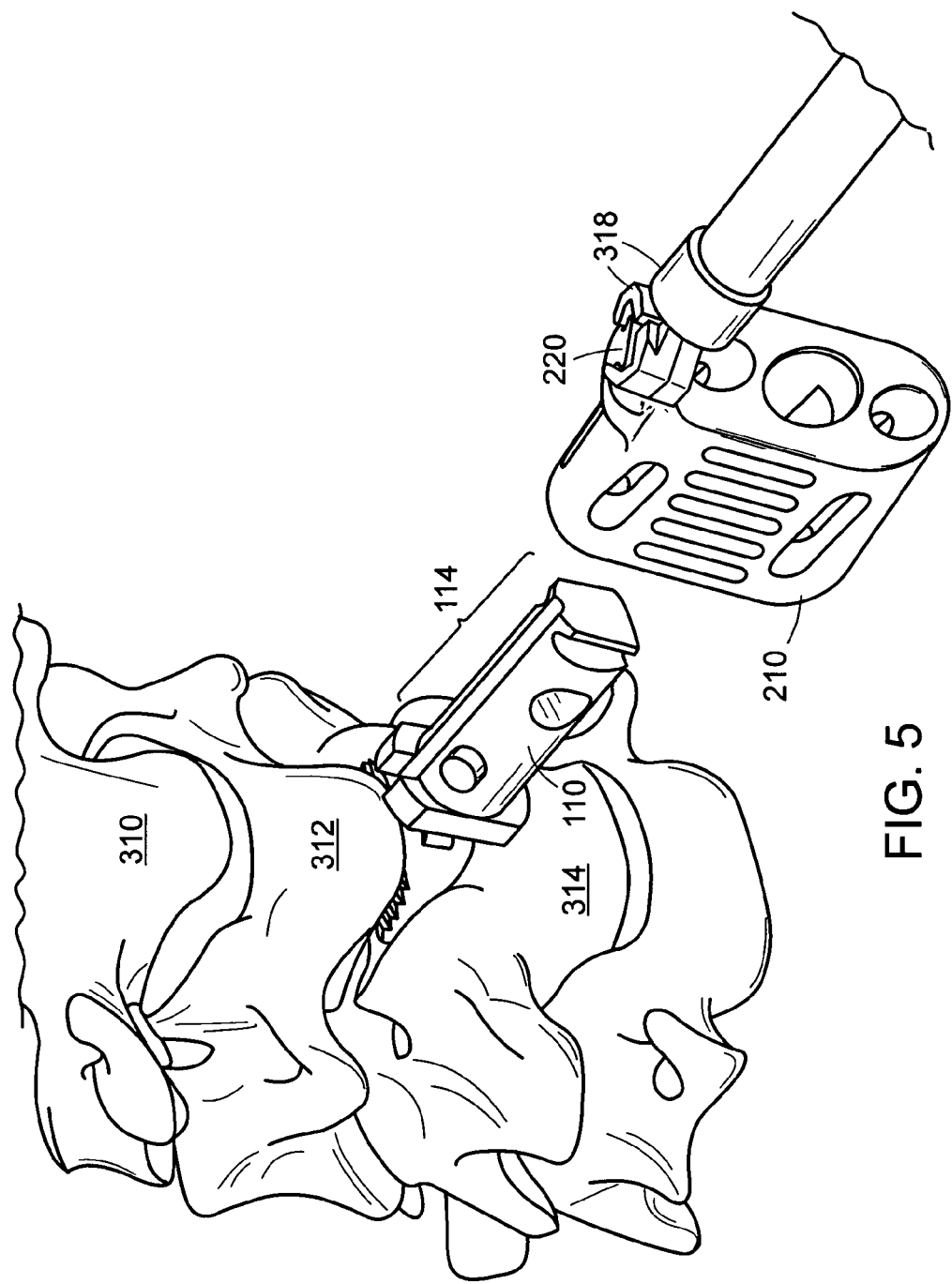
FIG. 5 illustrates positioning of a guide component onto the coupling member of the spacer component.
Figure 6:
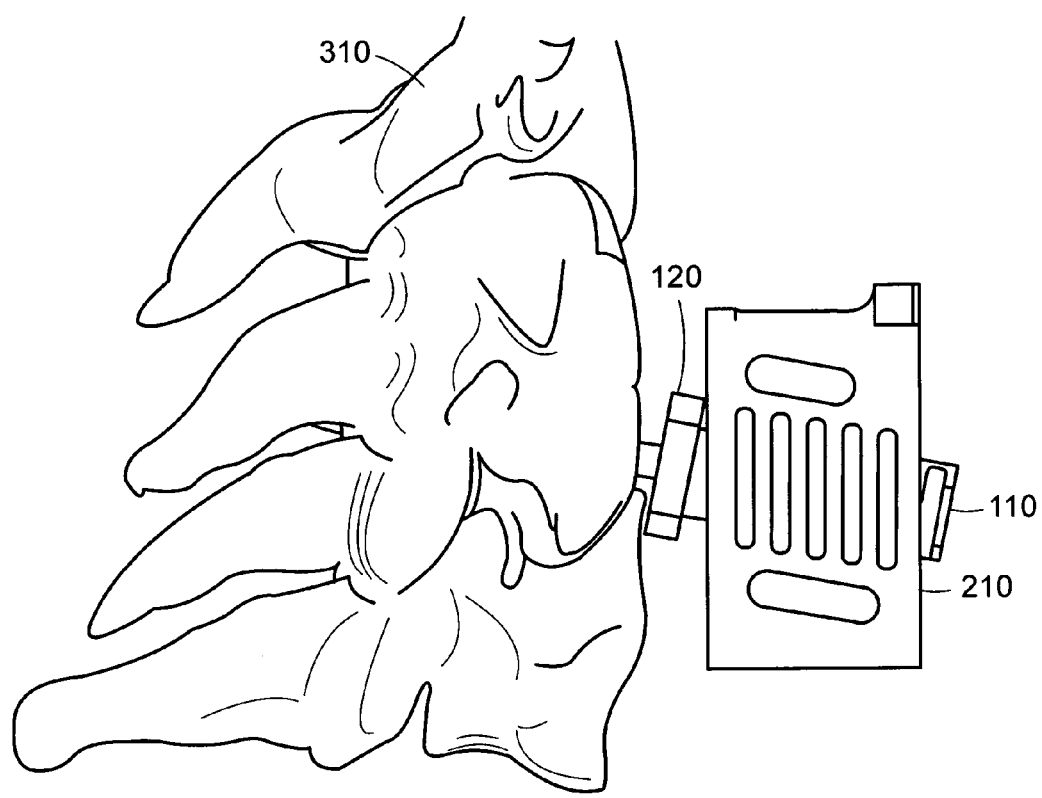
FIG. 6 shows a side view of a spacer component inserted into an intervertebral space and a guide component positioned on the coupling member of the spacer component.

The method for placing pins in adjacent vertebrae also includes the step of positioning the guide component onto the coupling member of the spacer component. FIG. 5 illustrates positioning of guide component 210 onto coupling member 114 of spacer component 110. Surgical instrument 318 can be used to grasp guide component 210 at instrument handle 220. Guide component 210 is then positioned on coupling member 110. FIG. 6 shows a side view of spacer component 110 inserted into the intervertebral space and guide component 210 positioned onto the coupling member of the spacer component. As shown, vertebral stop 120 can abut spinal column 310 and spacer component 210. In one embodiment, guide component 210 includes a substantially radiopaque orientation marker and the method for placing pins in adjacent vertebrae further includes the step of using fluoroscopy or x-ray and the orientation marker to determine the position of the guide component after positioning it on coupling member 110.

Figure 7:
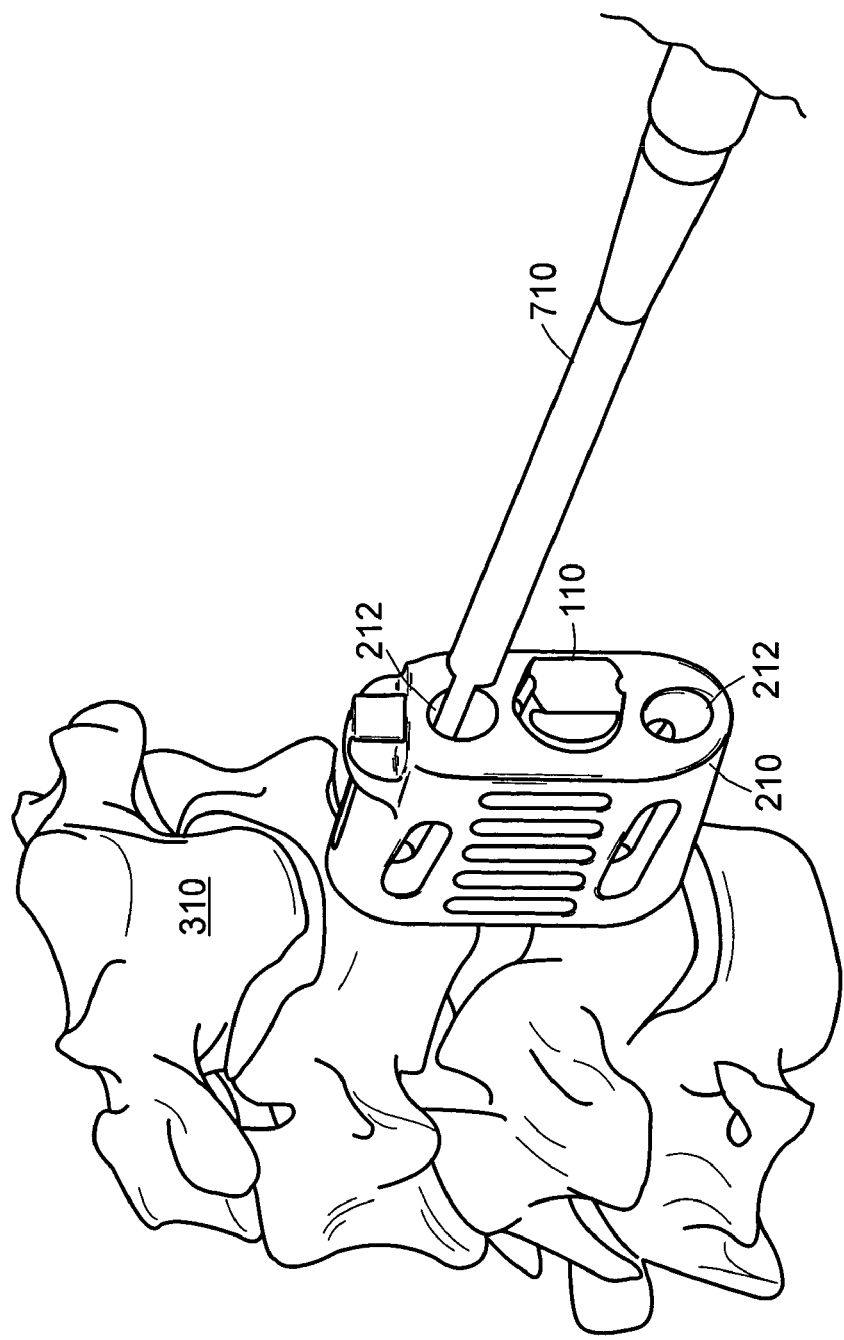
FIG. 7 illustrates use of an awl to prepare the vertebrae for placement of pins in the vertebrae.

The method for placing pins in adjacent vertebrae also includes the step of placing the pins in adjacent vertebrae through at least two of the plurality of parallel guide tubes. Placing pins in adjacent vertebrae can include preparing the adjacent vertebrae for placement of the pins. For example, preparing the adjacent vertebrae can include creating pilot holes using an awl or a drill. FIG. 7 illustrates the use of an awl to prepare the vertebrae for placement of pins in the vertebrae. Awl 710 can be inserted into each parallel guide tube 212 and used to prepare the vertebrae for placement of the pins.

Figure 8:
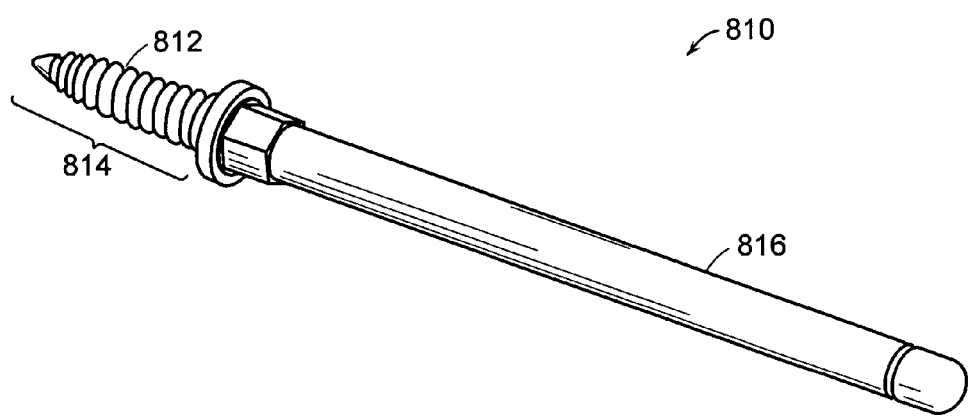
FIG. 8 is a perspective view of a pin suitable for use in the present invention.

FIG. 8 is a perspective view of a pin suitable for use in the present invention. Pin 810 includes threads 812, extending over a thread length 814, and pin shaft 816. Preferably, pin 810 is a distraction pin. Typically, pin 810 has a thread engagement length ranging from about 12 mm to about 16 mm.

Figure 9:
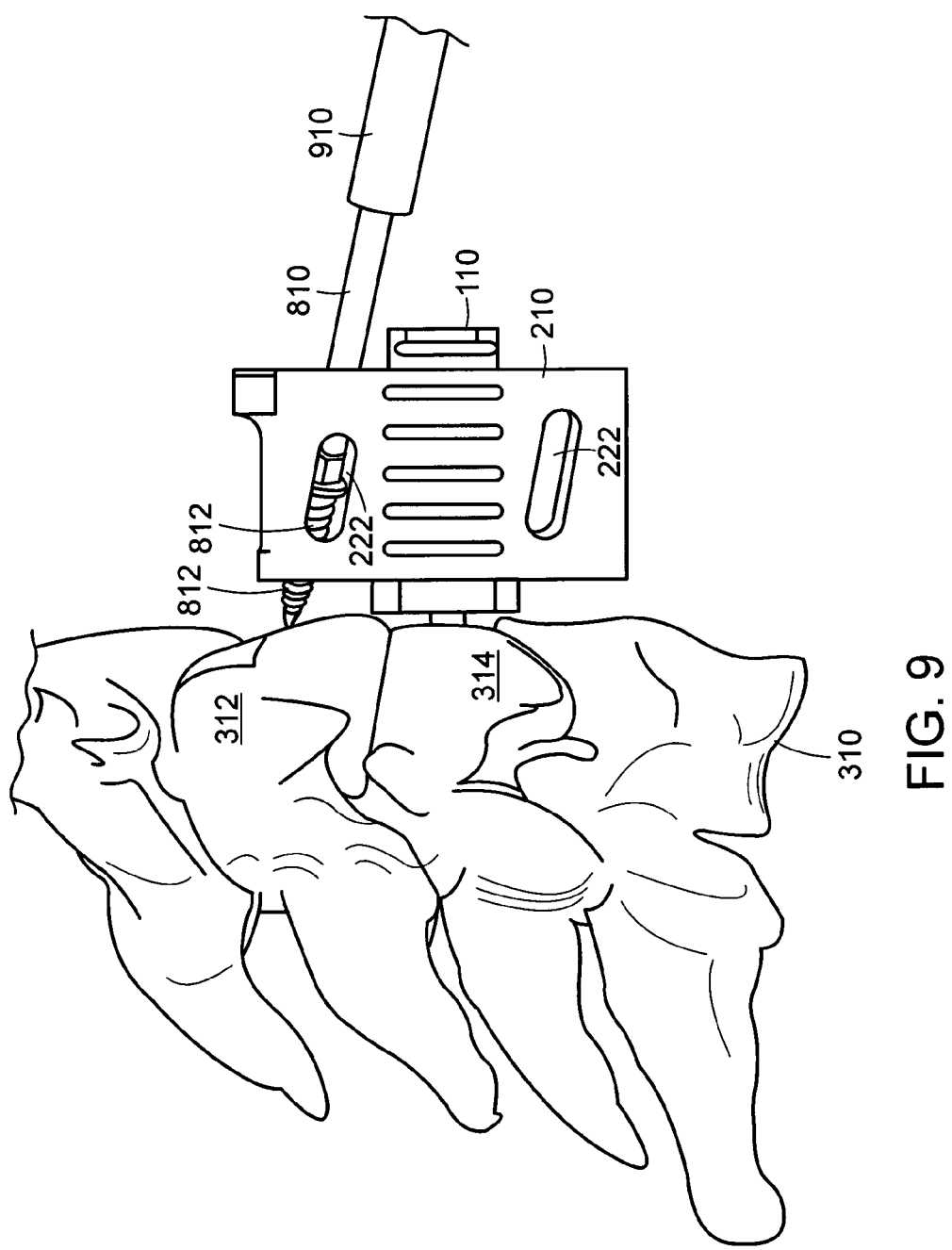
FIG. 9 illustrates use of a driver to place a pin into a vertebra using the modular pin guide of the present invention.

Placing pin 810 into superior vertebra 312 through parallel guide tube 212 is shown in FIG. 9. Pin 810 is inserted into parallel guide tube 212. Driver 910 is then used to screw pin 810 into superior vertebra 312. Guide window 222 can be used by the surgeon to determine the depth of an instrument or pin within parallel guide tube 212. By using guide window 222 to determine the position of an instrument or pin within parallel guide tube 212, the surgeon can avoid damaging the vertebra, for example, by avoiding over-tightening a threaded pin or stripping the vertebral bone. After first placing one pin, e.g., a superior positioned pin as illustrated in FIG. 9 or an inferior positioned pin, a second pin can be placed into a vertebra through another parallel guide tube 212.

Figure 10:
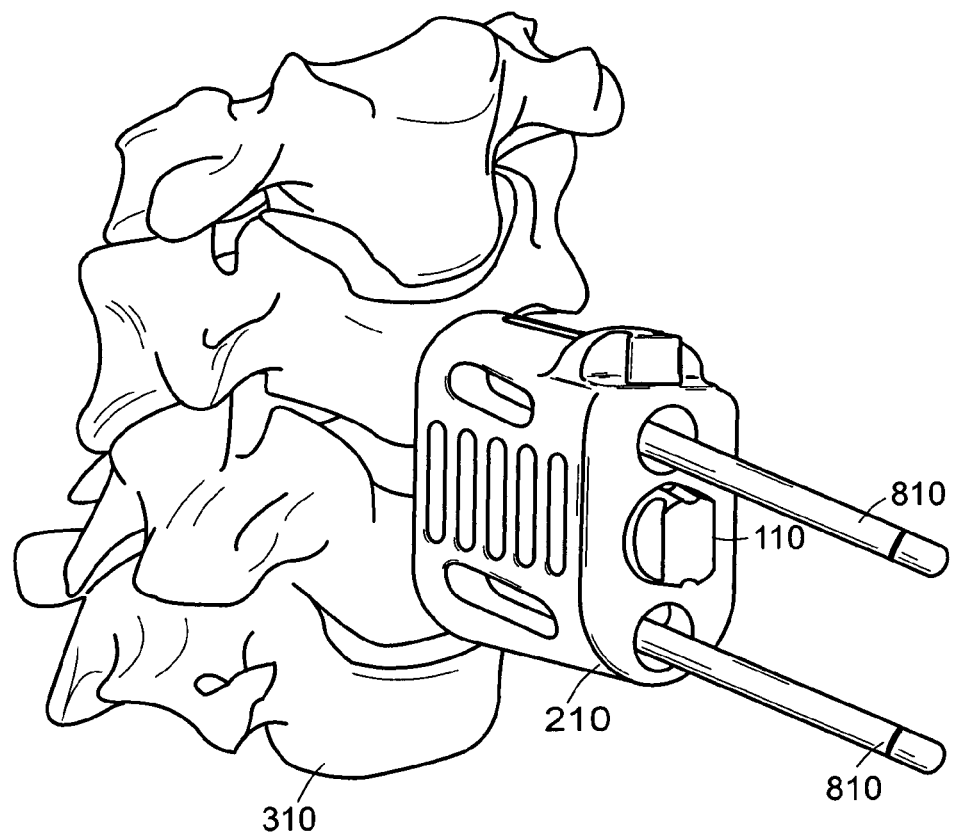
FIG. 10 shows pins placed in adjacent vertebrae using the modular pin guide of the present invention.
Figure 11:
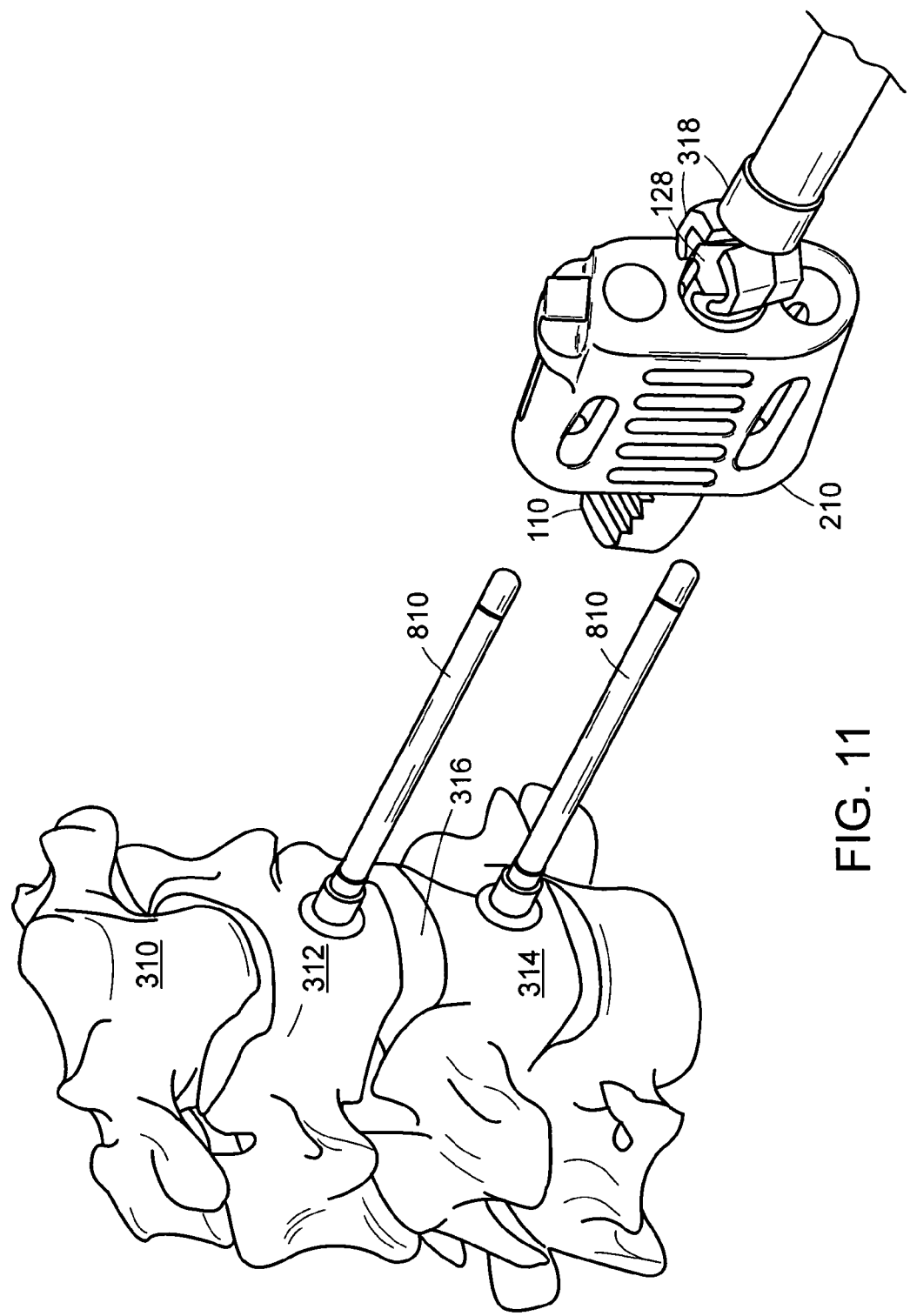
FIG. 11 illustrates removal of the modular pin guide from the placed pins.

FIG. 10 shows pins 810 placed in adjacent vertebrae parallel to the vertebrae endplates using the modular pin guide of the present invention. FIG. 11 illustrates removal of the modular pin guide from placed pins 810. In the illustrated embodiment, the modular pin guide is removed by grasping instrument handle 128 using surgical instrument 318 and pulling the modular pin guide from pins 810. Pins 810 are located in superior vertebra 312 and inferior vertebra 314, are aligned substantially parallel to each other and to the endplates of superior vertebra 312 and inferior vertebra 314, and are located midline of spinal column 310.

Figure 12:
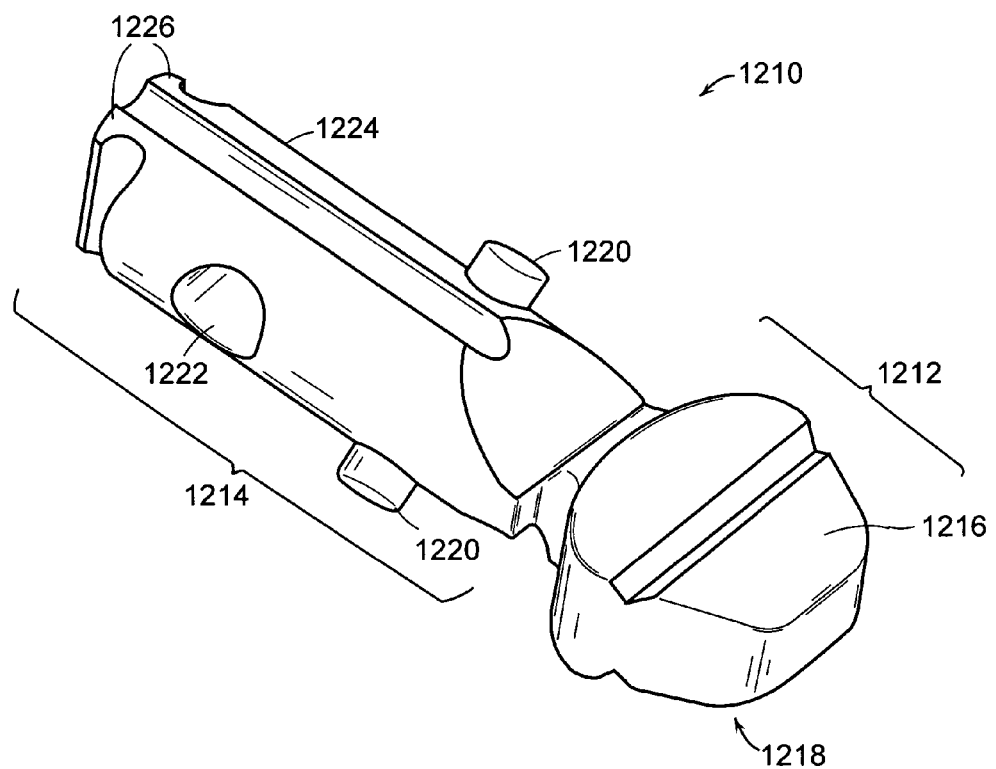
FIG. 12 is a perspective view of a modular pin guide spacer component without a vertebral stop in another embodiment of the present invention.

FIG. 12 illustrates a variation on spacer component 110 according to another embodiment of the present invention. Alternative spacer component 1210 differs principally from spacer component 110 described supra in that alternative spacer component 1210 does not contain a vertebral stop.

Spacer component 1210 includes intervertebral spacer 1212. Intervertebral spacer 1212 includes first surface 1216 and second surface 1218. FIG. 12 illustrates first surface 1216 and second surface 1218 having a groove thereon. In one embodiment, the groove is a reference marker, for example, that aligns with the center of rotation of the spinal column upon the desired positioning of the intervertebral spacer 1212 in the intervertebral space. In some embodiments, at least first surface 1216 or second surface 1218 includes a textured surface. The textured surface can include a patterned textured surface or the textured surface can have irregular texturing. In other embodiments, first surface 1216 and/or second surface 1218 are substantially smooth. First surface 1216 and second surface 1218 are preferably adapted for contact with adjacent vertebral bodies. As illustrated in FIG. 12, first surface 1216 and second surface 1218 of intervertebral spacer 1210 skew toward one another. In other embodiments not illustrated in FIG. 12, first surface 1216 and second surface 1218 are parallel or substantially parallel.

Spacer component 1210 also includes coupling member 1214, as described supra with respect to coupling member 114. As also described supra with respect to spacer component 110, spacer component 1210 can contain one or more anti-rotation elements 1220, orientation markers such as marker hole 1222 and marker groove 1224, and instrument handle 1226.

Figure 13:
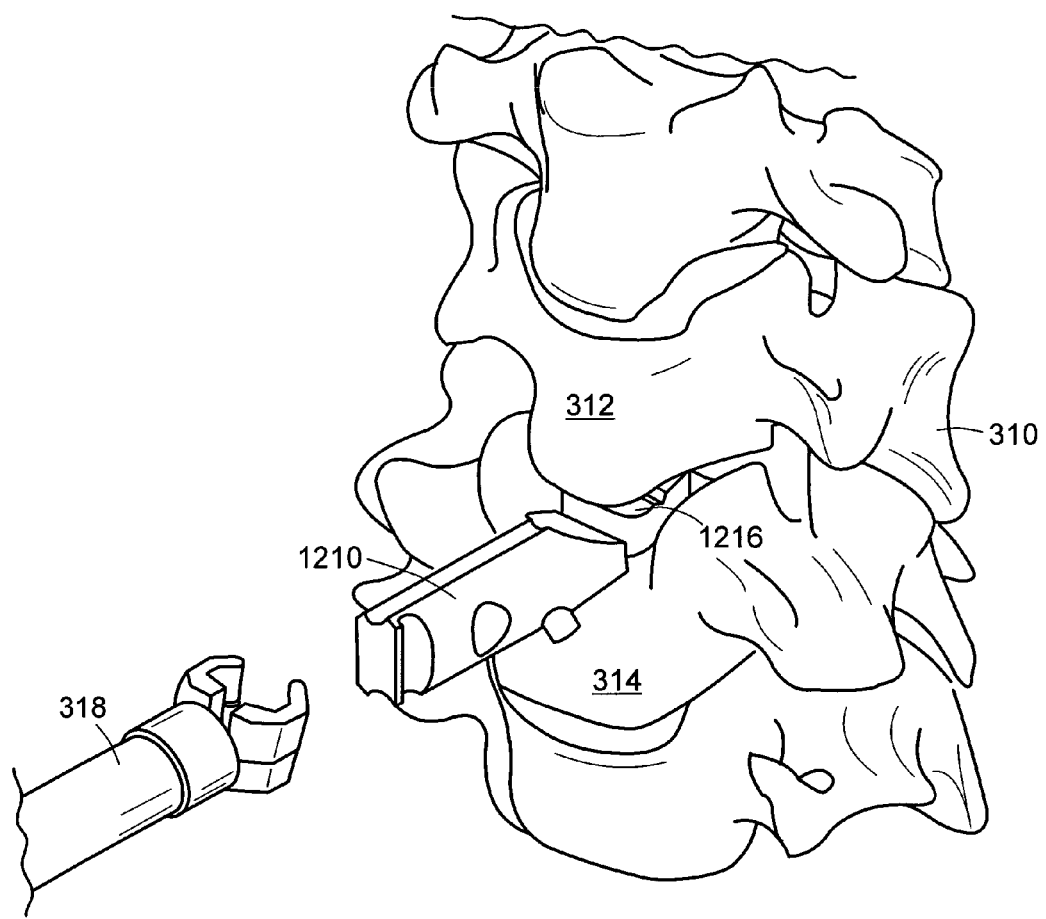
FIG. 13 illustrates insertion of a modular pin guide spacer component without a vertebral stop into an intervertebral space.

FIG. 13 illustrates the insertion of modular pin guide spacer component without a vertebral stop 1210 into an intervertebral space. In one embodiment, intervertebral spacer 1212 of spacer component 1210 is placed between superior vertebra 312 and inferior vertebra 314. Spacer component 1210 can be used to determine acceptable anterior/posterior positioning of an intervertebral spacer and suitable dimensions for an intervertebral spacer (e.g., footprint and height). For example, in one embodiment, spacer component 1210 is used to determine a suitably sized intervertebral spacer 116 that will be used to place pins 810 in the adjacent vertebrae as described supra. The method for placing pins in adjacent vertebrae described herein can include the step of positioning the guide component onto the coupling member of spacer component 1210. In one embodiment, the guide component contacts vertebra bone when positioned onto coupling member 1214 of spacer component 1210.

Also described herein is a pin guide comprising: (a) a support; (b) an intervertebral spacer projecting from the support; and (c) a plurality of parallel guide tubes defined by the support, wherein the parallel guide tubes are sized to align pins inserted into the guide tubes in a substantially parallel orientation. In one embodiment, the pin guide is a modular pin guide, for example, as described supra. In another embodiment, the pin guide is a one-piece guide.

Figure 14A:
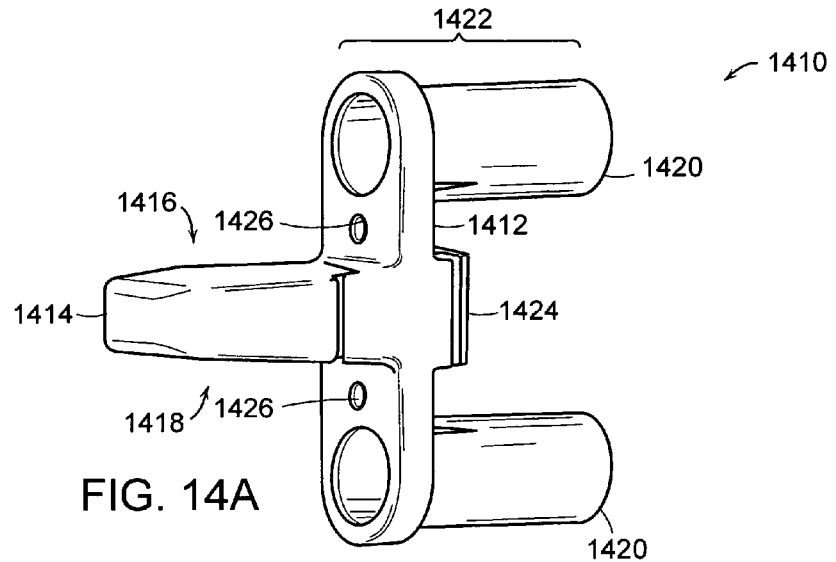
FIGS. 14A and 14B are perspective views of a pin guide according to another embodiment of the present invention.
Figure 14B:
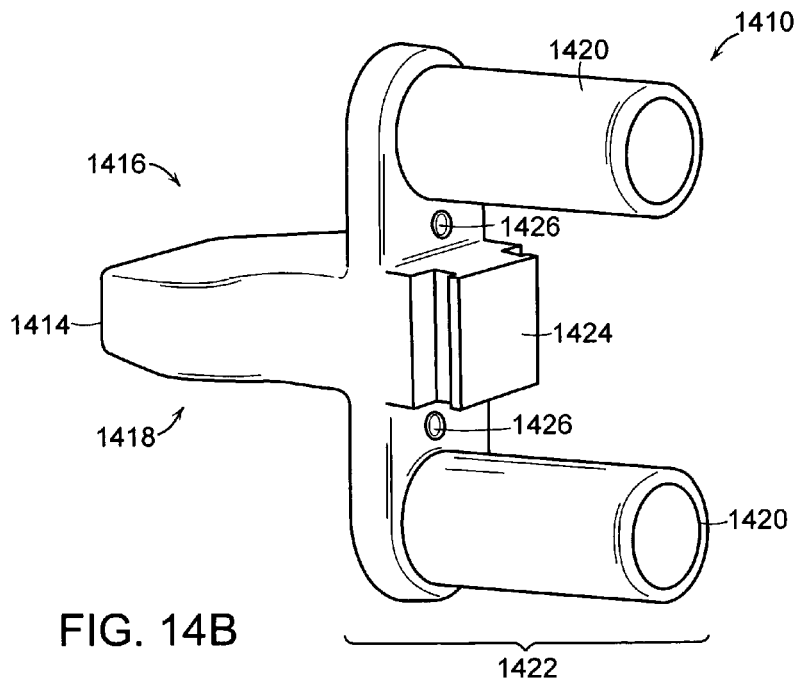

FIGS. 14A and 14B are perspective views of pin guide 1410 according to one embodiment of the present invention. Pin guide 1410 can be a modular pin guide or a one-piece guide. Pin guide 1410 includes support 1412. Support 1412 can be constructed of any material compatible with surgical procedures, for example, any material capable of sterilization and capable of withstanding stresses applied during use of the pin guide in surgery. In one preferred embodiment, support 1412 is constructed of a substantially radiopaque material such as, for example, radiopaque ceramic, stainless steel, titanium, tantalum cobalt, chromium, aluminum, and combinations thereof. In another embodiment, support 1412 is constructed of a substantially radiolucent material such as a substantially radiolucent plastic. In another embodiment, support 1412 is a composite of radiopaque and radiolucent materials. In one embodiment, support 1412 can act as a vertebral stop, described supra. In other embodiments, pin guide 1410 can further include a distinct vertebral stop component.

Pin guide 1410 also includes intervertebral spacer 1414. Intervertebral spacer 1414 projects from the support. In one embodiment, intervertebral spacer 1414 projects from support 1412 at a substantially right angle. In other embodiments, intervertebral spacer 1414 forms an acute angle with support 1412. In one embodiment, intervertebral spacer 1414 is removable from support 1412. In another embodiment, intervertebral spacer 1414 is permanently affixed to support 1412.

Intervertebral spacer 1414 includes first surface 1416 and second surface 1418. FIGS. 14A and 14B illustrate first surface 1416 and second surface 1418 having ridges thereon. In some embodiments, at least first surface 1416 or second surface 1418 includes a textured surface. The textured surface can include a patterned textured surface or the textured surface can have irregular texturing. First surface 1416 and second surface 1418 are preferably adapted for contact with adjacent vertebral bodies. As illustrated in FIGS. 14A and 14B, first surface 1416 and second surface 1418 of intervertebral spacer 1414 skew toward one another. In other embodiments not illustrated in FIGS. 14A and 14B, first surface 1416 and second surface 1418 are parallel or substantially parallel.

Intervertebral spacer 1414 can be supplied in a variety of dimensions depending on the particular surgical application. As described with respect to intervertebral spacer 112 supra, intervertebral spacer 1414 has a depth, width, and height. In some embodiments, depth can range from about 12 to about 16 millimeters (mm), width can range from about 14.5 to about 19 mm, and height can range from about 5 to about 10 mm. For example, intervertebral spacer 1414 can have a footprint of about 12 mm by about 14.5 mm, about 14 by about 17 mm, or about 16 mm by about 19 mm (depth by width). Intervertebral spacer 1414 can have height of, for example, about 5, 6, 7, 8, 9, or about 10 mm.

Pin guide 1410 also includes a plurality of parallel guide tubes 1420 extending through support 1412 wherein the parallel guide tubes are sized to align pins inserted into the guide tubes in a substantially parallel orientation. In one embodiment, parallel guide tubes extend through support 1412 and project in a direction opposite to intervertebral spacer 1414 as shown in FIGS. 14A and 14B. In a preferred embodiment, pin guide 1410 contains two parallel guide tubes 1420. In one embodiment, parallel guide tubes 1420 are substantially parallel to intervertebral spacer 1414. In one embodiment, parallel guide tube 1420 can define a guide window that can be used by the surgeon to determine the depth of an instrument or pin within parallel guide tube 1420.

Preferably, parallel guide tubes 1420 are of sufficient length and of sufficient diameter to maintain an inserted pin in alignment with the guide tube as the pin is placed into a vertebra. Parallel guide tubes have length 1422. In one embodiment, each of the parallel guide tubes 1420 has length 1422 greater than its diameter. In one embodiment, each of the parallel guide tubes 1420 has length 1422 at least equal to the thread engagement length of the pin to be inserted therein. In one embodiment, each of parallel guide tubes 1420 has a length of at least about 12 mm such as a length in the range of from at least about 12 mm to at least about 16 mm.

Pin guide 1410 also preferably includes instrument handle 1424. Instrument handle 1424 can be attached to support 1412 and is generally located distally to intervertebral spacer 1414. In one embodiment, instrument handle 1424 is adapted to be received by a general purpose surgical instrument. In one embodiment, instrument handle 1424 is a projection, for example, a projection molded or machined into support 1412. In one embodiment, instrument handle 1424 is a dovetailed projection as illustrated in FIGS. 14A and 14B.

Pin guide 1410 also can include orientation markers such as marker holes or marker grooves. In one embodiment, the orientation marker is a cylindrical marker hole. For example, the orientation marker can be a marker hole defined by the pin guide such as marker hole 1426 defined by support 1412. In one embodiment, at least a portion of support 1412 surrounding the orientation marker is radiopaque. The orientation marker can be of any size or shape whereby orientation of pin guide 1410 can be determined when fluoroscopy, x-ray, or eyesight is used to assess position of the pin guide.

Components of pin guide 1410 such as intervertebral spacer 1414, parallel guide tubes 1420, and instrument handle 1424 can be constructed of any of the materials suitable for use in support 1412, described supra. For example, in one embodiment, pin guide 1410 is entirely constructed of a substantially radiopaque material such as stainless steel or titanium. In other embodiments, pin guide 1410 is a composite of radiolucent and radiopaque materials.

The present invention also includes a method for placing pins in adjacent vertebrae. The method comprises the steps of: (a) positioning between adjacent vertebrae an intervertebral spacer of the pin guide that includes a support; the intervertebral spacer projecting from the support; and a plurality of parallel guide tubes extending through the support, wherein the parallel guide tubes are sized to align pins inserted into the guide tubes in a substantially parallel orientation; and (b) placing pins in the adjacent vertebrae through at least two of the plurality of parallel guide tubes.

Figure 15:
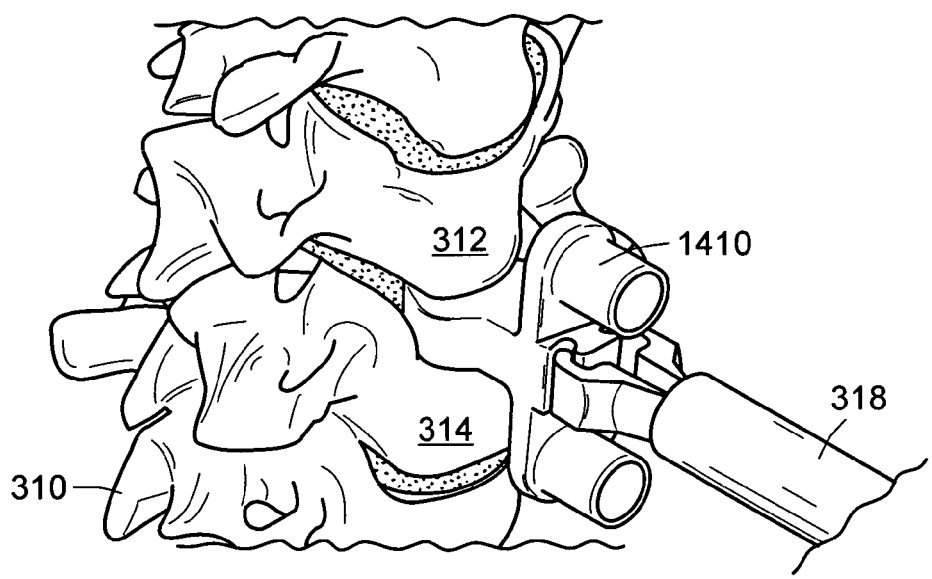
FIG. 15 illustrates insertion of a pin guide into an intervertebral space.

FIG. 15 includes an anterior view of spinal column 310 and illustrates the positioning of intervertebral spacer 1414 of pin guide 1410 between adjacent vertebrae 312 and 314. Spinal column 310 includes superior vertebra 312 and inferior vertebra 314 which enclose an intervertebral space. Thus, FIG. 15 shows the insertion of intervertebral spacer 1414 into the intervertebral space. Surgical instrument 318 can be used to grasp pin guide 1410 at instrument handle 1424. In one embodiment, pin guide 1410 includes a substantially radiopaque orientation marker and the method for placing pins in adjacent vertebrae further includes the step of using fluoroscopy or x-ray and the orientation marker to determine the position of the spacer component after positioning intervertebral spacer 1414 between the adjacent vertebrae.

Figure 16:
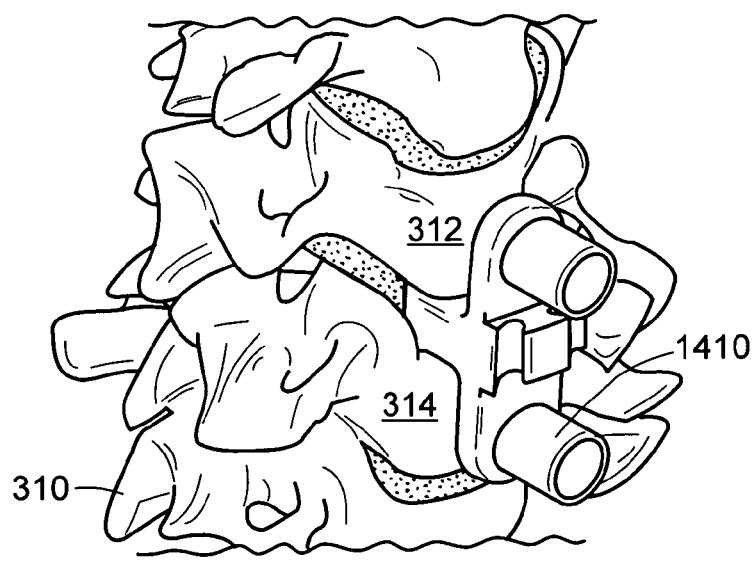
FIG. 16 shows a pin guide inserted into the intervertebral space.

In one embodiment, the method includes the additional step of removing an intervertebral disc or a portion of an disc from between the adjacent vertebrae, e.g., superior vertebra 312 and inferior vertebra 314, prior to positioning intervertebral spacer 1414 between those adjacent vertebrae. FIG. 16 shows intervertebral spacer 1414 of pin guide 1410 positioned between adjacent vertebrae, superior vertebra 312 and inferior vertebra 314.

Pin guide 1410 can be selected from among a group of pin guides each having an intervertebral spacer 1414 of a particular dimension. Surgeons can select a pin guide 1410 having a particular dimensioned intervertebral spacer 1414 depending on such circumstances as, for example, the location and size of the particular intervertebral space of interest. Examples of suitable sizes for intervertebral spacers are described supra.

Figure 17:
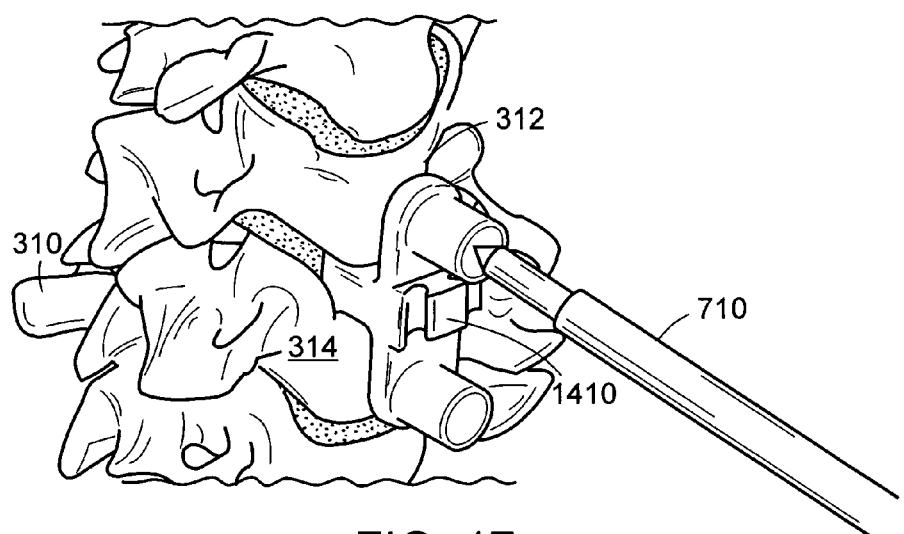
FIG. 17 illustrates use of an awl instrument to prepare the vertebrae for placement of pins in the vertebrae.

The method for placing pins in adjacent vertebrae also includes the step of placing the pins in adjacent vertebrae through at least two of the plurality of parallel guide tubes. Placing pins in adjacent vertebrae can include preparing the adjacent vertebrae for placement of the pins. For example, preparing the adjacent vertebrae can include creating pilot holes using an awl or a drill. FIG. 17 illustrates the use of an awl to prepare the vertebrae for placement of pins in the vertebrae. Awl 710 can be inserted into each of parallel guide tubes 1420 and used to prepare the vertebrae for placement of the pins.

Figure 18:
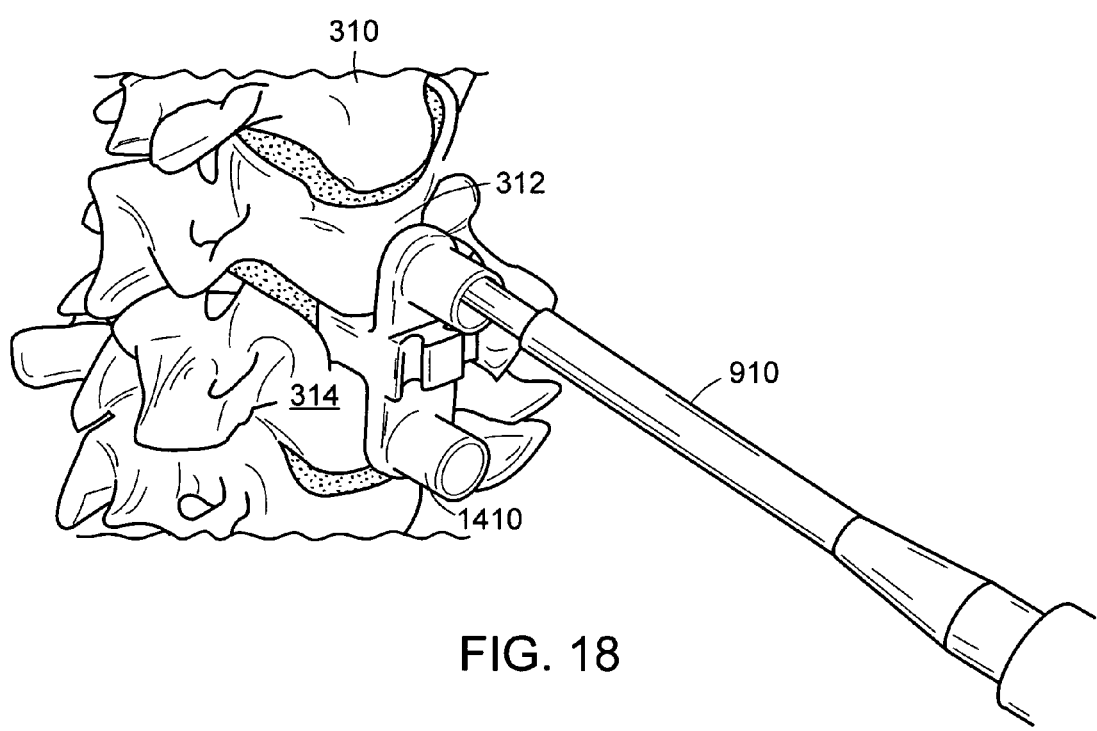
FIG. 18 illustrates use of a driver instrument to place a pin into a vertebra using the pin guide of the present invention.

Placing pin 810 into superior vertebra 312 through parallel guide tube 1420 is shown in FIG. 18. Pin 810 is inserted into parallel guide tube 1420. Driver 910 is then used to screw pin 810 into superior vertebra 312. In one embodiment, a guide window (not illustrated) defined by parallel guide tube 1420 can be used by the surgeon to determine the depth of an instrument or pin within the parallel guide tube. After first placing one pin, e.g., a superior positioned pin as illustrated in FIG. 18 or an inferior positioned pin, a second pin can be placed into a vertebra through another parallel guide tube 1420.

Pins suitable for use in the present invention include pin 810 of FIG. 8. As described supra, pin 810 includes threads 812, extending over a thread length 814, and pin shaft 816. Preferably, pin 810 is a distraction pin. Typically, pin 810 has a thread engagement length ranging from about 12 mm to about 16 mm.

Figure 19:
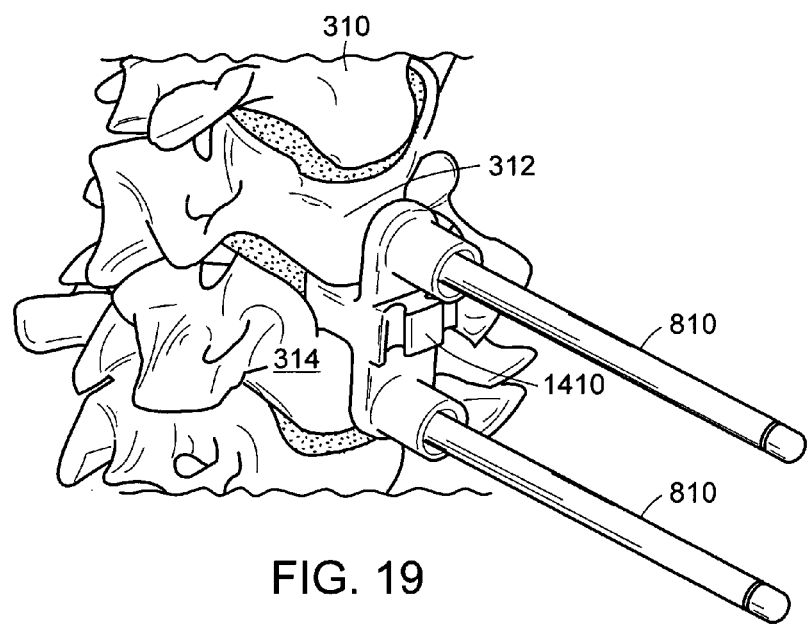
FIG. 19 shows pins placed in adjacent vertebrae, prior to removal of the pin guide, using the pin guide of the present invention.
Figure 20:
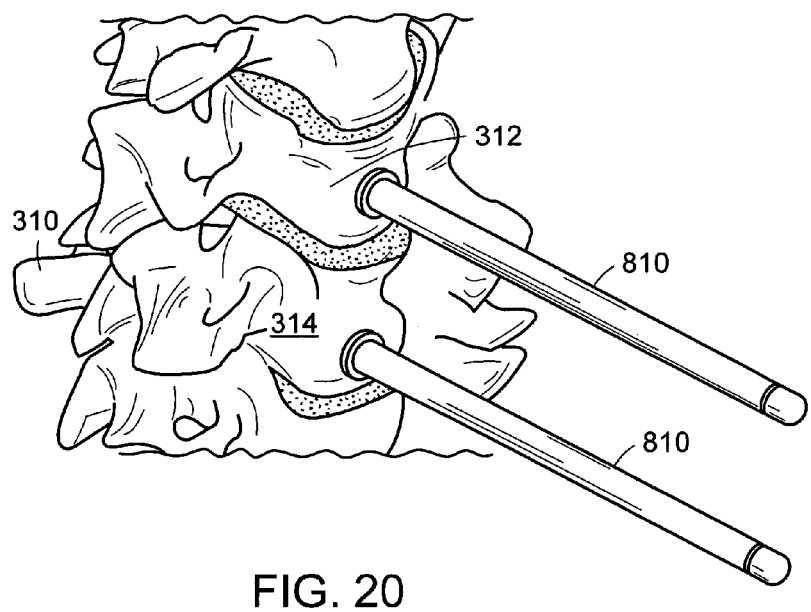
FIG. 20 shows pins placed in adjacent vertebrae, after removal of the pin guide, using the pin guide of the present invention.

FIG. 19 shows pins 810 placed in adjacent vertebrae using pin guide 1410, prior to removal of the pin guide. Pin guide 1410 is typically removed by grasping instrument handle 1424 using surgical instrument 318 and pulling the pin guide from pins 810. FIG. 20 shows pins 810 placed in adjacent vertebrae, after removal of the pin guide. Pins 810 are located in superior vertebra 312 and inferior vertebra 314, are aligned substantially parallel to each other and to the endplates of superior vertebra 312 and inferior vertebra 314, and are located midline of spinal column 310.

The present invention also includes an intervertebral implant insertion and alignment instrument, a distraction instrument, an intervertebral implant insertion guide, and methods for inserting an implant into an intervertebral space. Despite existing tools and techniques, present positioning of implants in intervertebral spaces often depends on a surgeon's skill, experience and technique. Practice of the present invention can aide in the placement of an implant into an intervertebral space, e.g., midline to the coronal plane spine and/or parallel to vertebral endplates that abut the intervertebral space. Practice of the present invention is suitable for, for example, the placement of implants into an intervertebral space such as those implants typically used in spinal fusion surgery and disc replacement surgery.

Figure 21B:
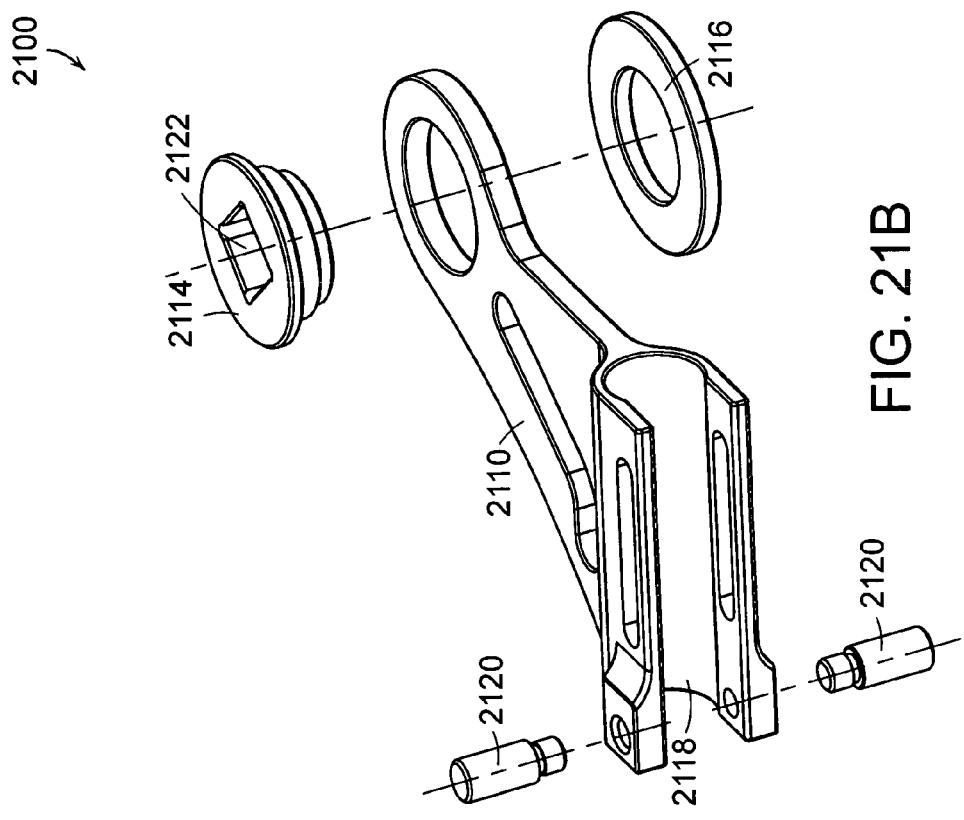
FIGS. 21A-21C illustrate an intervertebral implant insertion and alignment instrument according to one embodiment of the present invention.
Figure 21A:
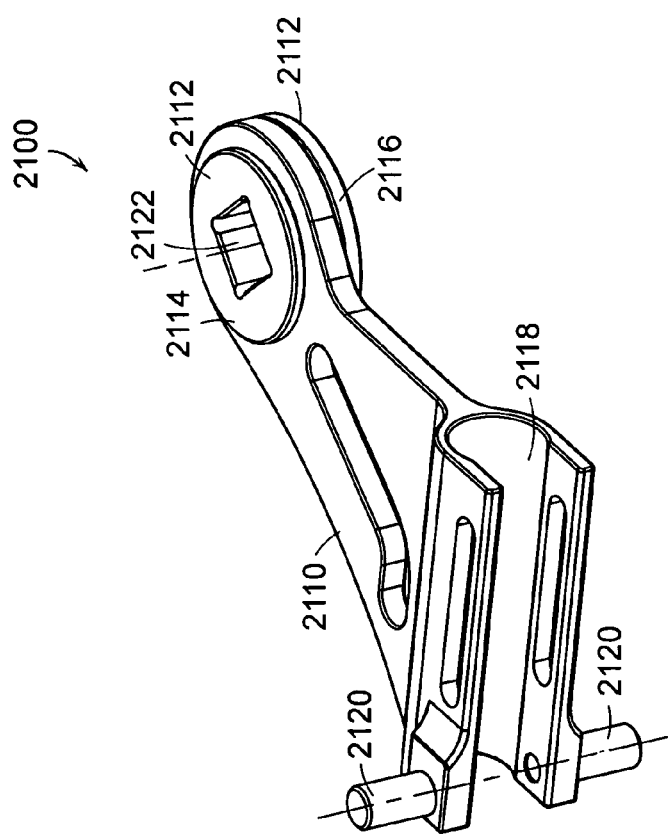
Figure 21C:
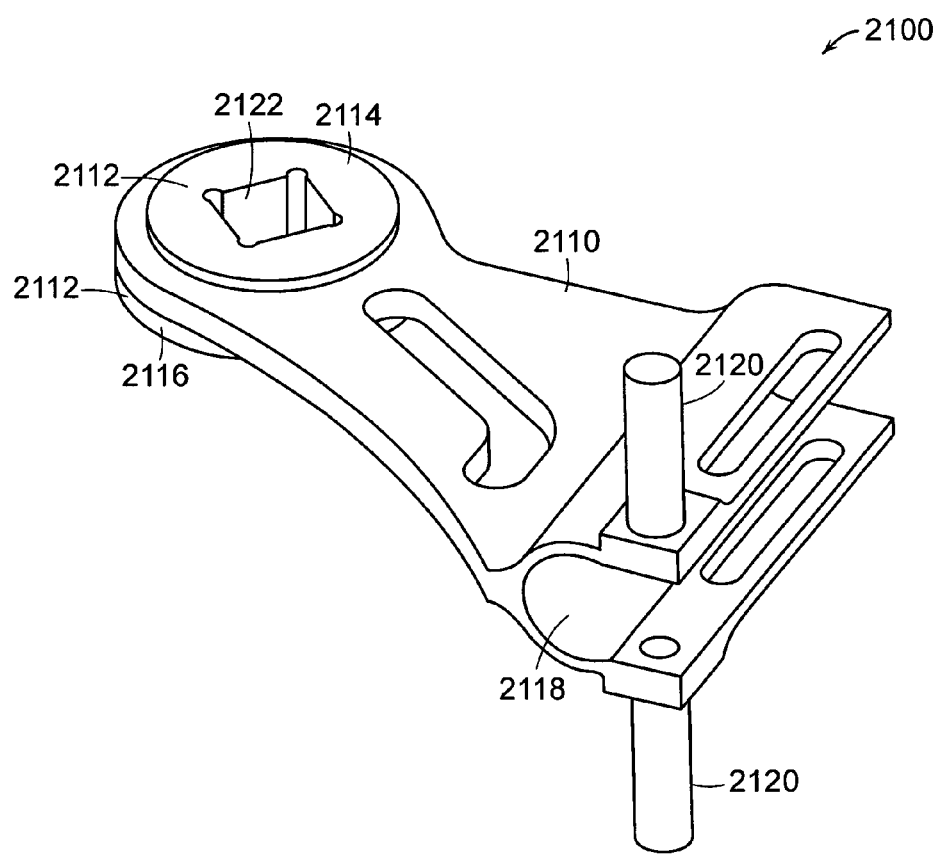

FIGS. 21A-21C illustrate intervertebral prosthetic implant insertion and alignment instrument 2100 according to one embodiment of the present invention. Instrument 2100 includes body 2110, rotatable bearing fixture 2112 including bearing 2114 and fastening cap 2116, cannular instrument guide 2118, and stop pins 2120. Rotatable bearing fixture 2112 defines opening 2122 for receiving a shaft of a distraction instrument. Opening 2122 can have any shape necessary to receive a shaft of a distraction instrument. For example, opening 2122 can have a rectangular cross-section. In one embodiment, opening 2122 has a square cross-section.

In one embodiment, cannular instrument guide 2118 defines a space, e.g., a cylindrical shaped space, wherein an intervertebral implant inserter can be positioned. As illustrated in FIGS. 21A-21C, cannular instrument guide 2118 has a general C-shape. Implant inserters suitable for use with the present invention and cannular instrument guide characteristics for accommodating the implant inserters are described infra.

In one embodiment, intervertebral implant insertion and alignment instrument 2100 includes at least one stop pin 2120. In some embodiments, not illustrated in FIGS. 21A-21C, intervertebral implant insertion and alignment instrument 2100 contains more than two stop pins 2120. In other embodiments, intervertebral implant insertion and alignment instrument 2100 does not include stop pins 2120.

Figure 22:
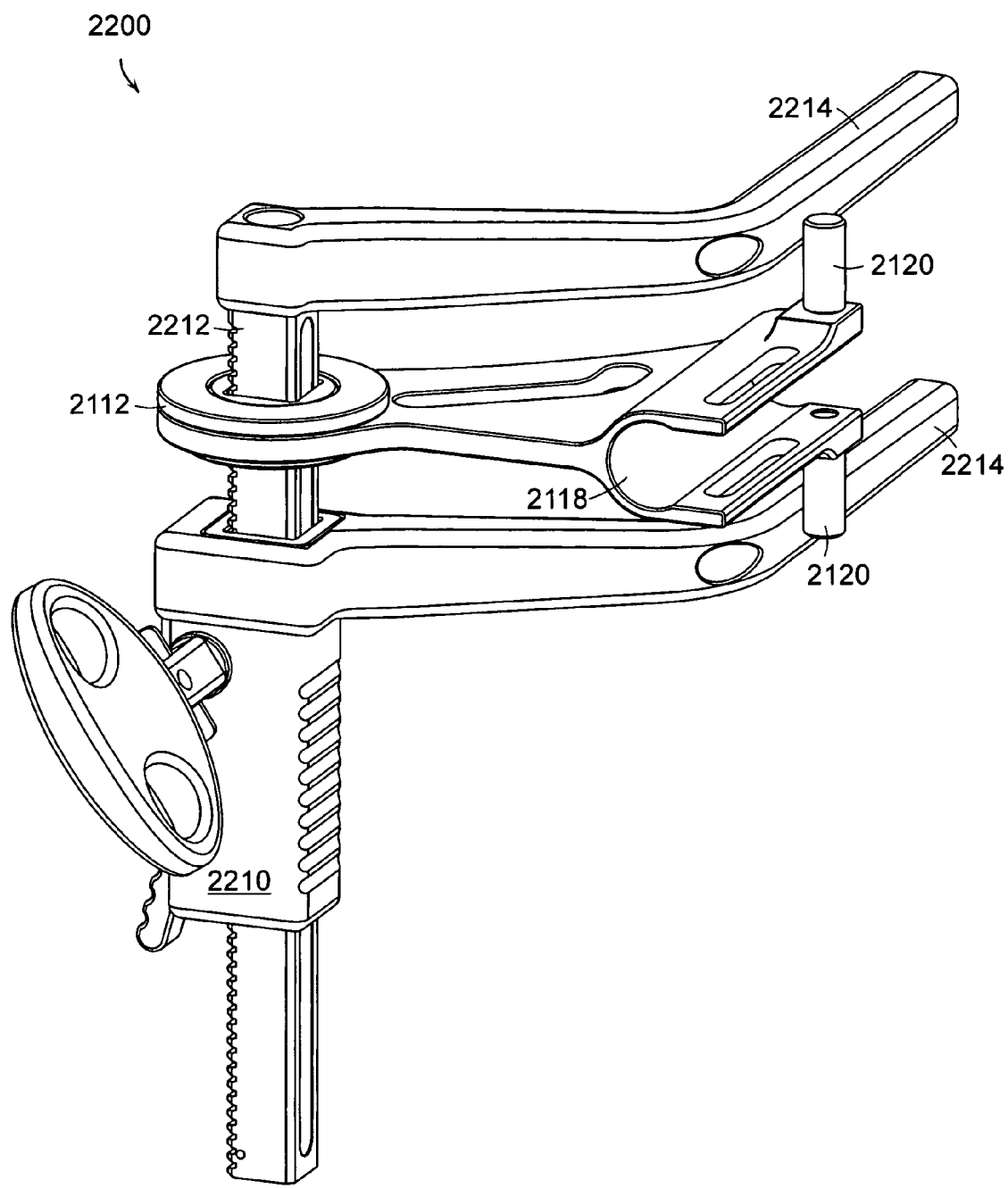
FIG. 22 shows, according to one embodiment, an intervertebral implant insertion and alignment instrument that includes a distraction instrument.

FIG. 22 shows intervertebral implant insertion and alignment instrument 2200 according to one embodiment of the present invention. Intervertebral implant insertion and alignment instrument 2200 is illustrated as rotatable bearing fixture 2112 and cannular instrument guide 2118 coupled with a distraction instrument, vertebral distractor 2210, e.g., a Caspar vertebral distractor. Vertebral distractor 2210 includes shaft 2212 and distraction arms 2214. Rotatable bearing fixture 2112 and cannular instrument guide 2118 can be coupled to vertebral distractor 2210 via opening 2122 defined by rotatable bearing fixture 2112. In one embodiment, the distraction instrument includes a shaft, e.g., shaft 2212, that is received by opening 2122. As illustrated in FIG. 22, vertebral distractor 2210 includes shaft 2212 that is square in cross-section and opening 2122 also has a square cross-section. In one embodiment, intervertebral implant insertion and alignment instrument 2200 is free to move along shaft 2212, e.g., in the superior and inferior directions.

FIG. 22 illustrates an embodiment wherein cannular instrument guide 2118 is positionable between arms 2214. Cannular instrument guide 2118 can be rotated via rotatable bearing fixture 2112 to which it is coupled. In one embodiment, at least one stop pin 2120 is included in intervertebral implant insertion and alignment instrument 2200. As illustrated, stop pin 2120 can extend laterally from cannular instrument guide 2118, whereby stop pin 2120 contacts arm 2214 upon rotation of cannular instrument guide 2118 via coupled rotatable bearing fixture 2112, thereby positioning cannular instrument guide 2118 for insertion of an implant. In other embodiments not illustrated in FIG. 22, the rotatable bearing fixture 2112 includes a stop feature whereby, upon rotation of cannular instrument guide 2118 via coupled rotatable bearing fixture 2112, cannular instrument guide 2118 can be positioned for insertion of an implant.

FIG. 23 shows implant inserter 2300 suitable for use with the present invention. Implant inserter 2300 includes shaft 2310. Shaft 2310 can be adapted to be received by cannular instrument guide 2118. Shaft 2310 is generally cylindrical. In some embodiments, however, shaft 2310 can be rectangular or any of a number of other shapes. In one embodiment, portion 2312 of implant inserter shaft 2310 has a reduced diameter, as compared to other portions, such as portions 2314 and 2316, of implant inserter shaft 2310, whereby implant inserter 2300 can be received by cannular instrument guide 2118.

By reducing the diameter of a portion of shaft 2310 or by flattening a portion of shaft 2310, the implant inserter can be received by cannular instrument guide 2118 and the implant inserter can be snugged into the cannular instrument guide by sliding the implant inserter within the cannular instrument guide. For example, the portion of shaft 2310 having a reduced diameter, e.g., portion 2312, can be aligned with cannular instrument guide 2118 and therein positioned. The implant inserter then can be snugged into cannular instrument guide 2118 by sliding the implant inserter within the cannular instrument guide. By sliding implant inserter 2300 within cannular instrument guide 2118 a portion of shaft 2310 having a larger diameter, e.g., portion 2314, can be moved into cannular instrument guide 2118, thereby aligning and snugging implant inserter 2300 within cannular instrument guide 2118. Thus, in one embodiment, the inside diameter of cannular instrument guide 2118 is larger than the diameter of implant inserter shaft portion 2313 and nearer the diameter of implant inserter shaft portion 2314 while still permitting implant inserter 2300 to slide within cannular instrument guide 2118.

In other embodiments, not shown in FIG. 23, a portion of implant inserter shaft 2310 is flattened, whereby the implant inserter can be received by the cannular instrument guide. For example, shaft 2310 can be flattened on a portion of at least one side to facilitate positioning into cannular instrument guide 2118. In another embodiment, shaft 2310 is flattened on a portion of two opposing sides to facilitate positioning into cannular instrument guide 2118.

In one embodiment, the present invention also includes a method for inserting an implant into an intervertebral space. FIGS. 1-11 illustrate the placement of pins into adjacent vertebrae which abut the intervertebral space. In one embodiment, distraction pins are placed into a vertebra midline to the spine. In another embodiment, distraction pins are placed into a vertebra parallel to an endplate of the vertebra that abuts the intervertebral space. In a preferred embodiment, a distraction pin is placed into a vertebra midline to the spine and parallel to an endplate of the vertebra that abuts the intervertebral space.

Figure 24A:
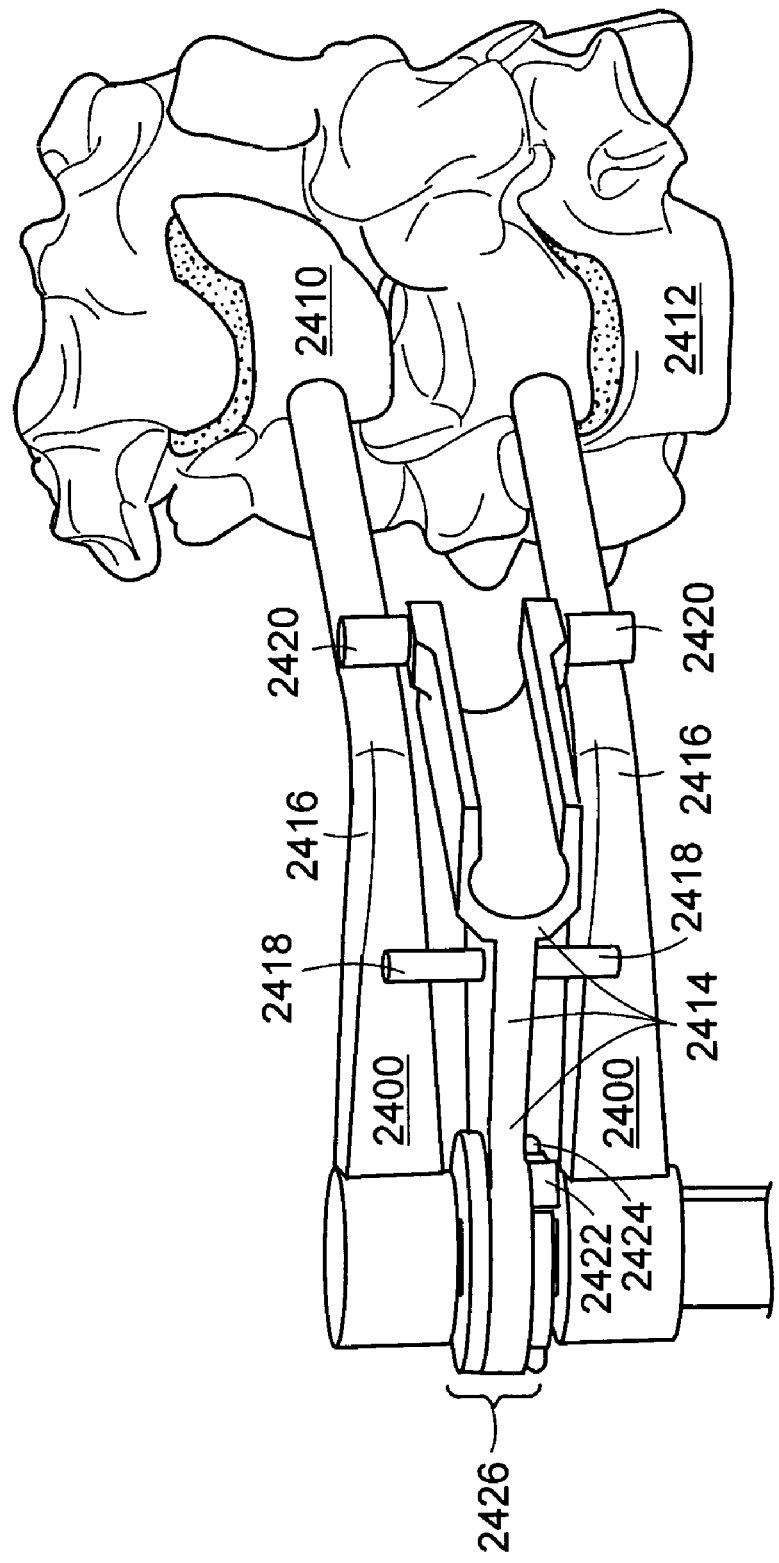
FIGS. 24A and 24B illustrate a distraction instrument and an intervertebral implant insertion and alignment instrument.

FIG. 24A shows distraction instrument 2400 placed onto distraction pins placed into adjacent vertebrae 2410 and 2412. Intervertebral implant insertion and alignment instrument 2414 is shown positioned between arms 2416 of distraction instrument 2400. As shown in FIG. 24A, intervertebral implant insertion and alignment instrument 2414 includes stop pins 2418 and 2420. In other embodiments, only stop pins 2420 are present. Distraction instrument 2400 is illustrated as a Casper vertebral distractor, but in other embodiments not illustrated, distraction instrument 2400 can be another distraction instrument to which intervertebral implant insertion and alignment instrument 2414 can be coupled.

Figure 24B:
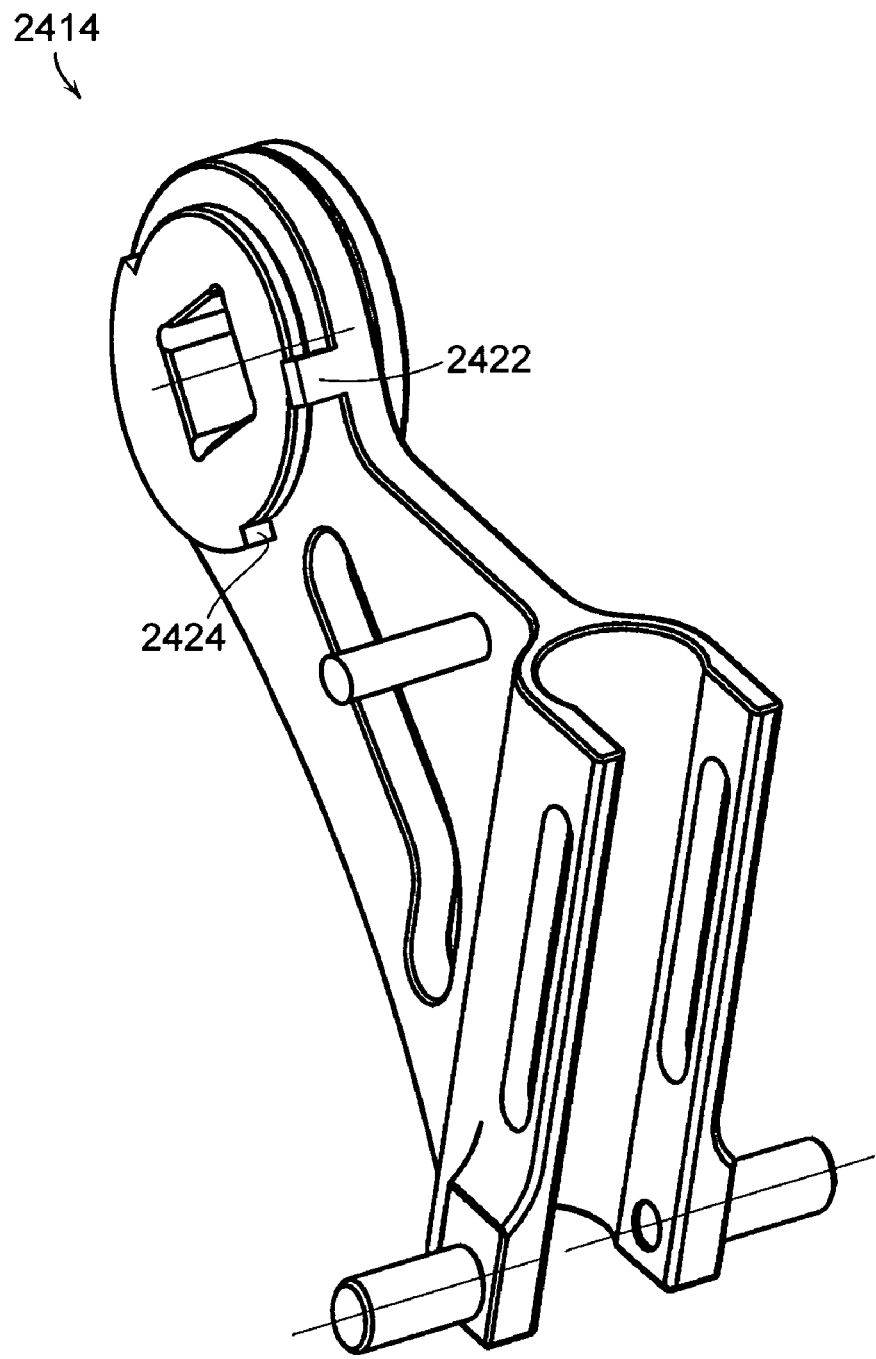

As illustrated in FIGS. 24A and 24B, intervertebral implant insertion and alignment instrument 2414 includes optional rotation stop feature 2422 which, when co-acting with stop feature 2424 of rotatable bearing 2426, can position cannular instrument guide 2118 for insertion of an implant. In one embodiment not illustrated, optional rotation stop feature 2422 and stop feature 2424 are used in lieu of stop pins 2418 and 2420 to position cannular instrument guide 2118 for insertion of an implant. Optional rotation stop feature 2422 and stop feature 2424 can also be used to limit the rotation range of cannular instrument guide 2118 about the shaft of the distraction instrument, e.g., to prevent intervertebral implant insertion and alignment instrument 2414 from contacting soft tissue during a surgical procedure.

Figure 25A:
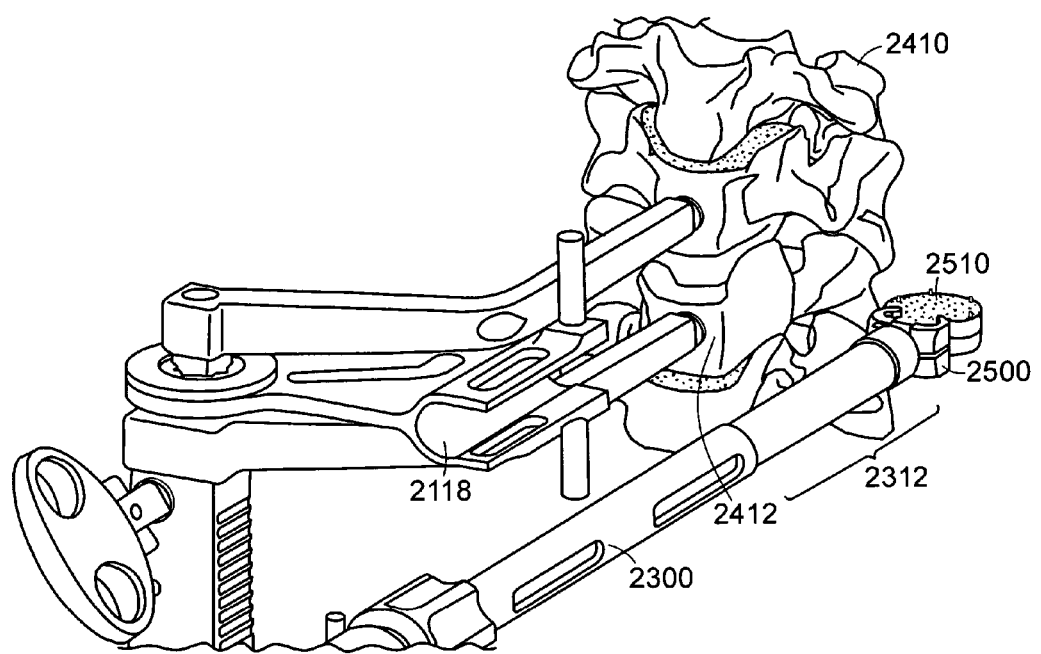
FIGS. 25A-25D show placement of an implant inserter instrument into a cannular instrument guide of an intervertebral implant insertion and alignment instrument.
Figure 25B:
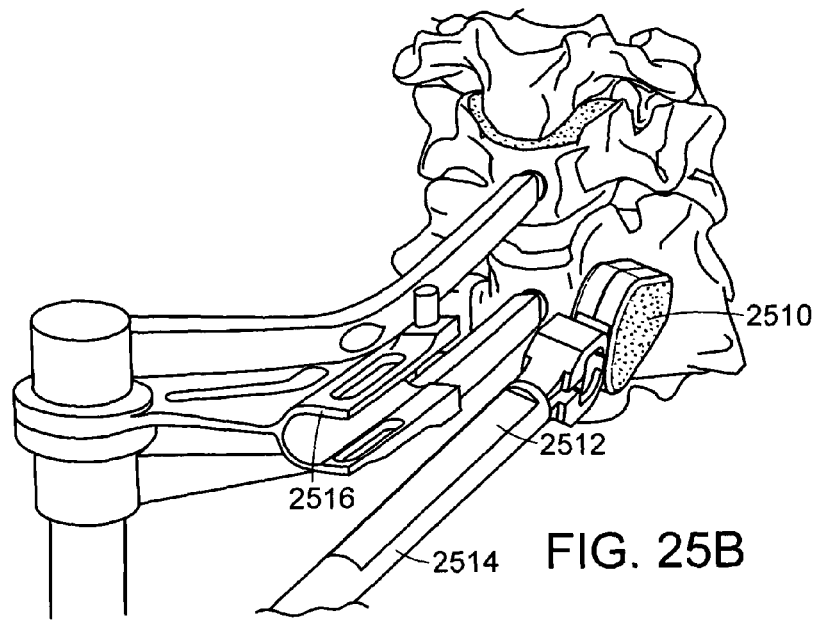
Figure 25C:
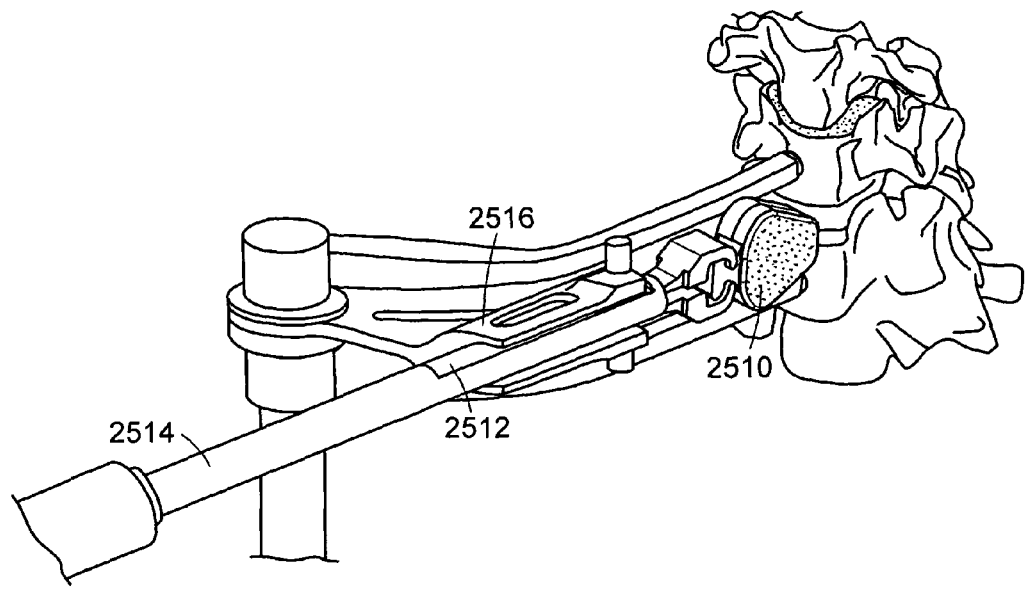
Figure 25D:
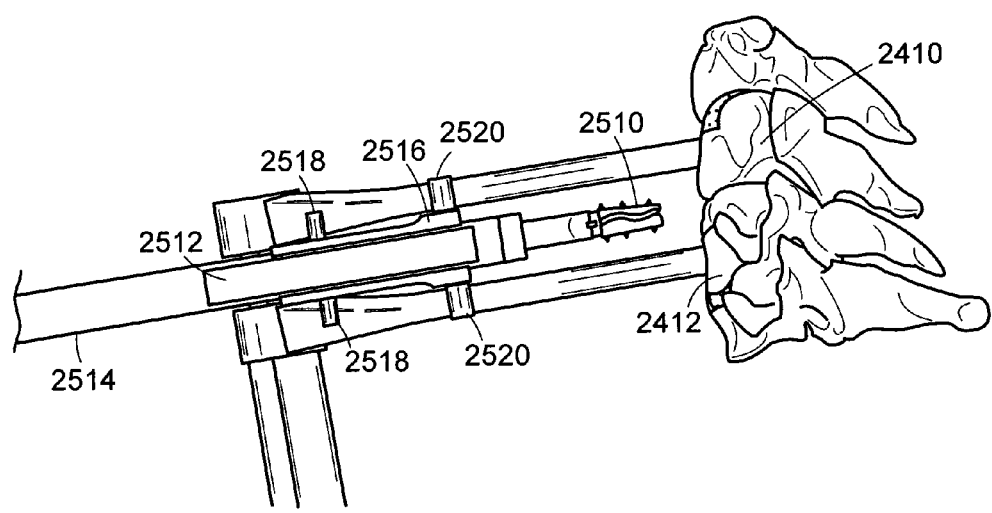

FIGS. 25A-25D show placement of implant insertion instrument 2300 into cannular instrument guide 2118. As shown in FIG. 25A, portion 2312 of implant inserter shaft 2310 having a reduced diameter can be positioned with respect to cannular instrument guide 2118 so that implant inserter 2300 can be received by cannular instrument guide 2118. As illustrated in FIG. 25A, implant inserter 2300 includes implant grasping mechanism 2500 holding implant 2510, e.g., a prosthetic disc. FIGS. 25B to 25D show an alternative embodiment in which a portion 2512 of implant inserter shaft 2514 is flattened, as described supra, whereby the implant inserter can be received by cannular instrument guide 2516. As shown in FIG. 25B, the intervertebral implant insertion and alignment instrument includes stop pins 2518 and 2520. In other embodiments, only stop pins 2520 are present or no stop pins are present.

Implant 2510 can then be inserted into the intervertebral space between vertebrae 2410 and 2412, wherein the implant insertion instrument is guided by the cannular instrument guide, for example, by sliding the implant insertion instrument within the cannular instrument guide.

Once implant 2510 is correctly inserted into the intervertebral space, implant 2510 can be released from grasping mechanism 2500. In one embodiment, implant 2510 can be inserted into the intervertebral space midline to the spine. In other embodiments, implant 2510 can be inserted into the intervertebral space parallel to the endplates of the vertebrae that abut the intervertebral space. In some embodiments, implant 2510 can be inserted into the intervertebral space midline to the spine and parallel to the endplates of the vertebrae that abut the intervertebral space.

Figure 26A:
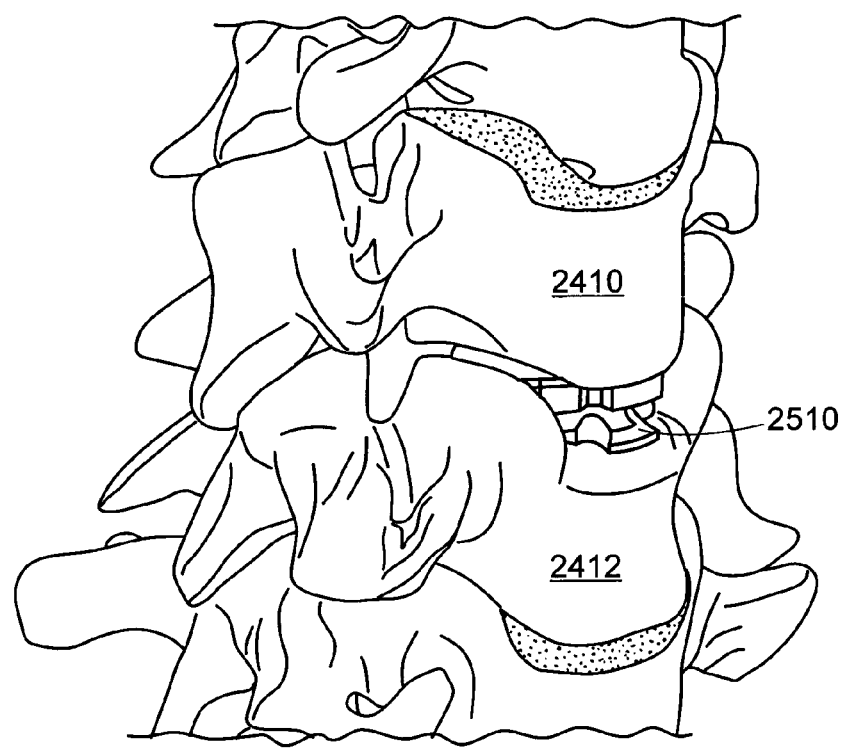
FIGS. 26A and 26B show an implant positioned in the intervertebral space between adjacent vertebrae.
Figure 26B:
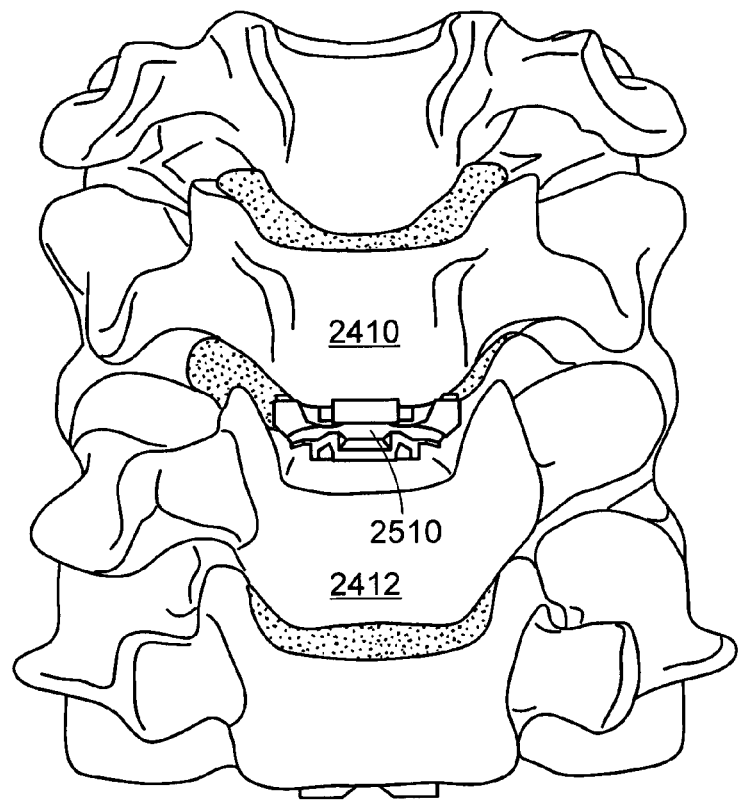

FIGS. 26A and 26B show implant 2510 positioned in the intervertebral space between adjacent vertebrae 2410 and 2412.

In one embodiment, the method for inserting an implant into an intervertebral space typically further includes the step of preparing the intervertebral space for an implant prior to inserting the implant. Preparing the intervertebral space for an implant can include a partial or complete discectomy. In one embodiment, preparing the intervertebral space for an implant can include distraction of vertebrae, e.g., distraction of the adjacent vertebrae.

Figure 27:
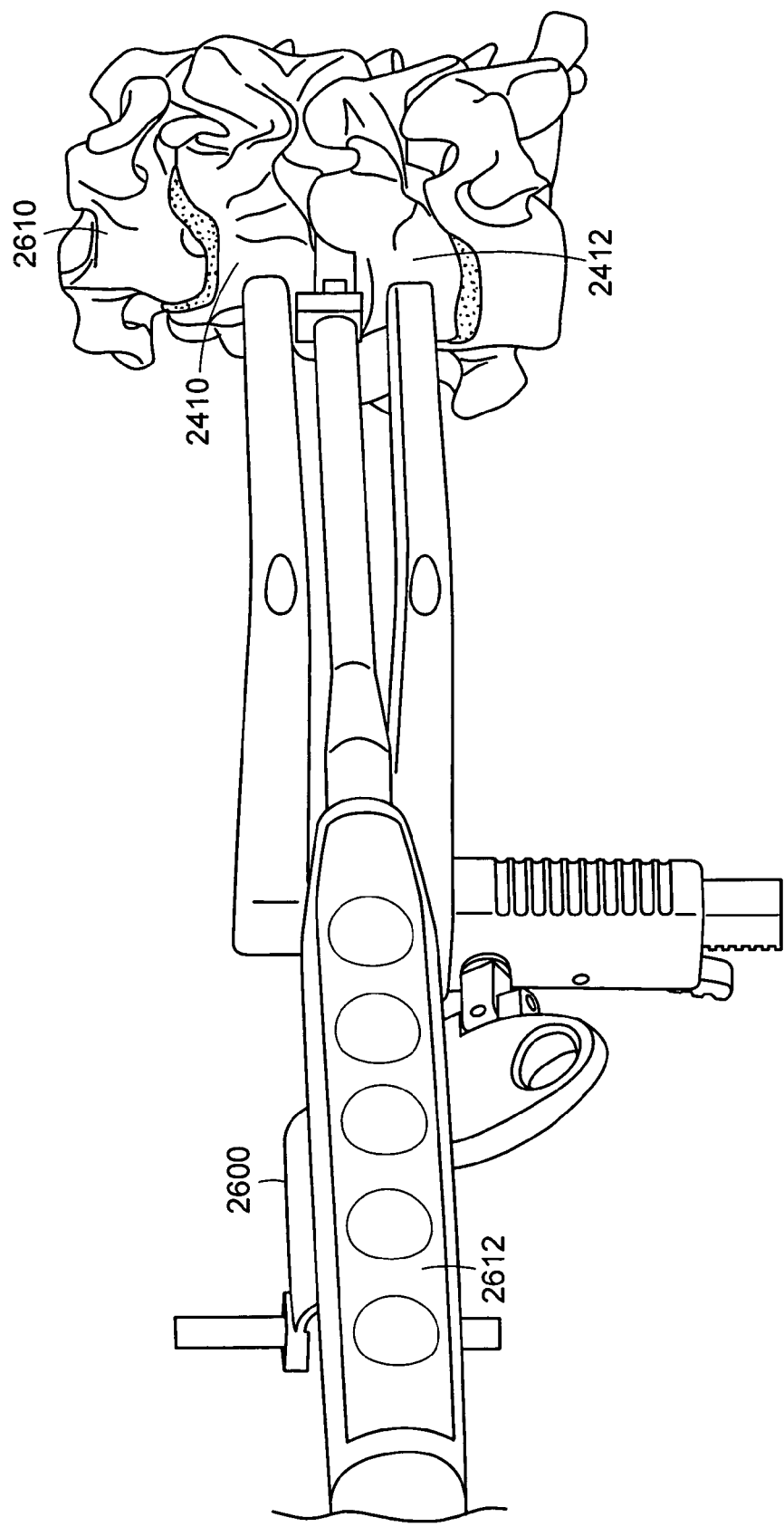
FIG. 27 illustrates preparation of an intervertebral space for an implant following placement of a distraction instrument that includes a cannular instrument guide.

In one embodiment, illustrated in FIG. 27, the intervertebral space can be prepared after placing a distraction instrument, wherein the distraction instrument includes cannular instrument guide 2600, onto distraction pins placed into adjacent vertebrae 2410 and 2412. As illustrated in FIG. 27, cannular instrument guide 2600 can be rotated away from the spinal column 2610 to allow access to the intervertebral space using instruments such as rasp 2612.

Figure 28:
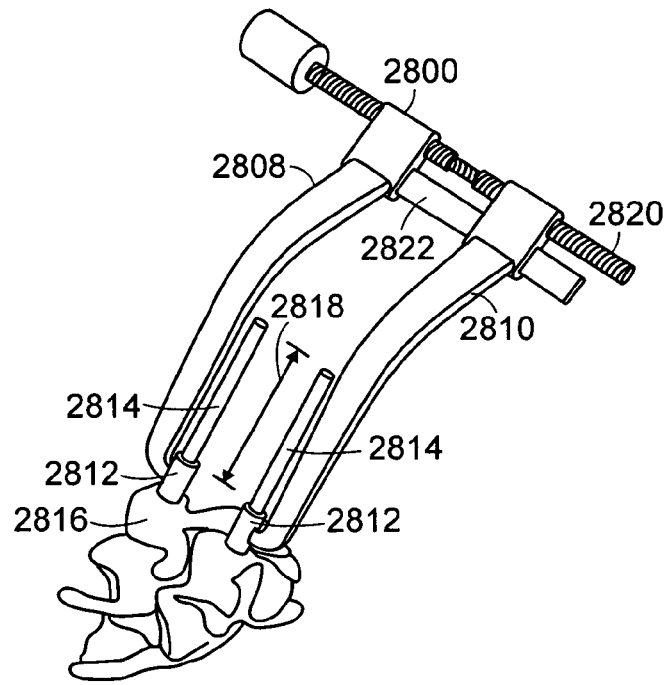
FIG. 28 illustrates a distraction instrument according to one embodiment of the present invention.
Figure 29A:
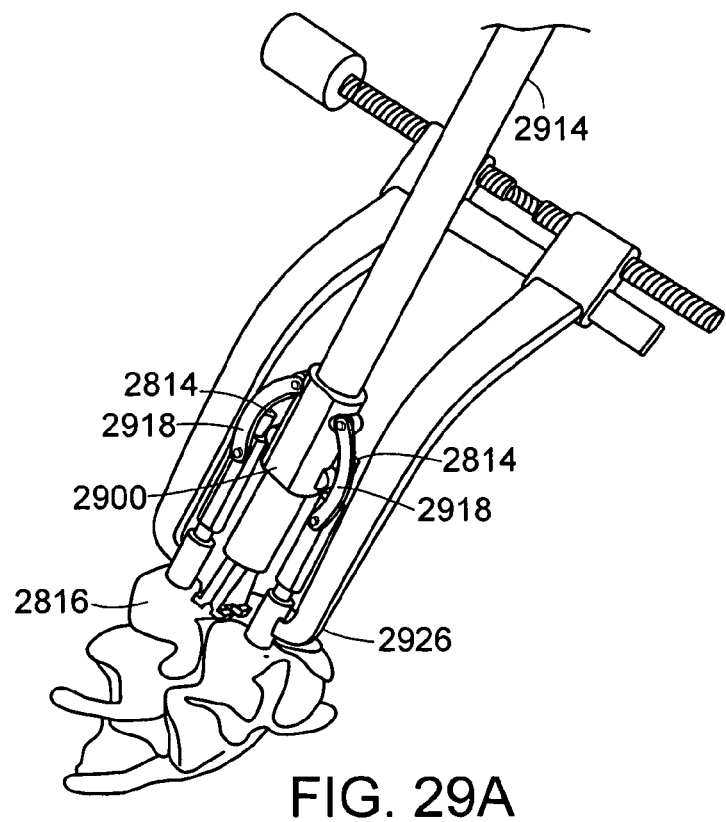
FIGS. 29A-29E illustrate an intervertebral implant insertion guide according to one embodiment of the present invention.
Figure 29B:
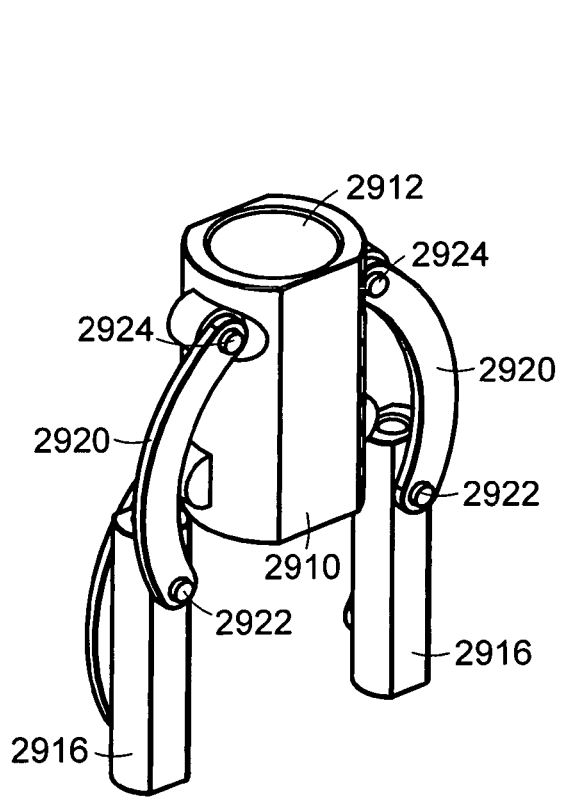
Figure 29C:
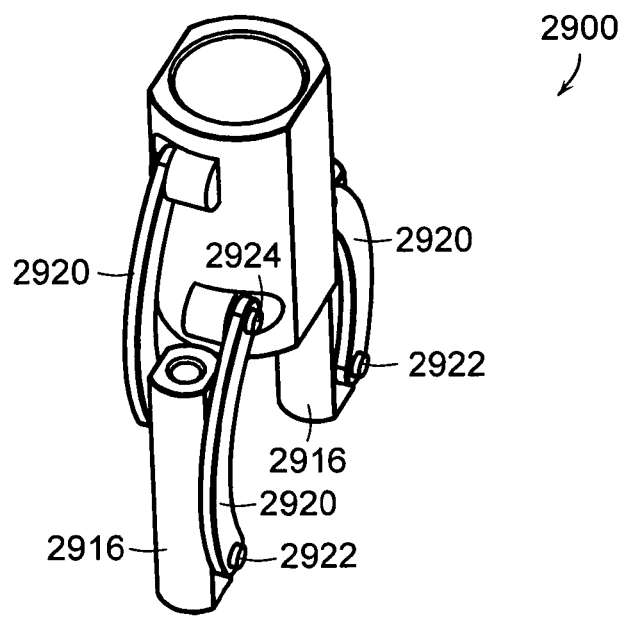
Figure 29D:
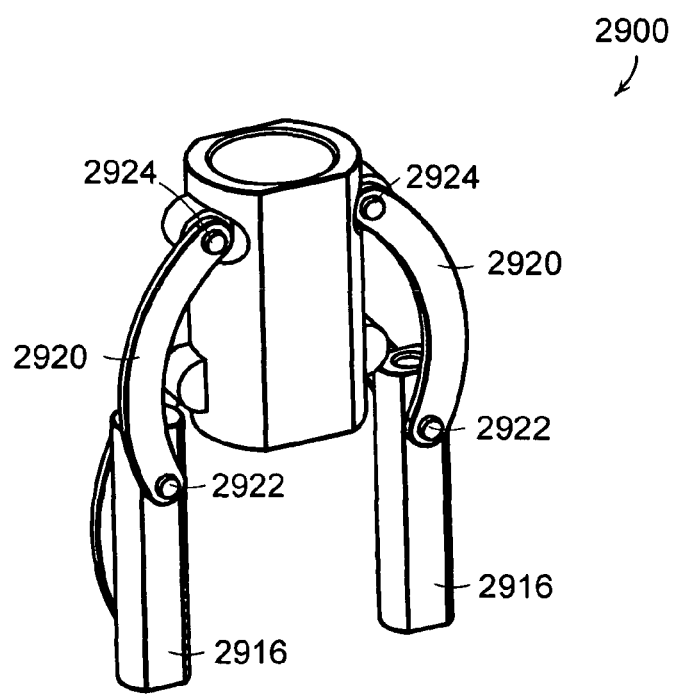
Figure 29E:
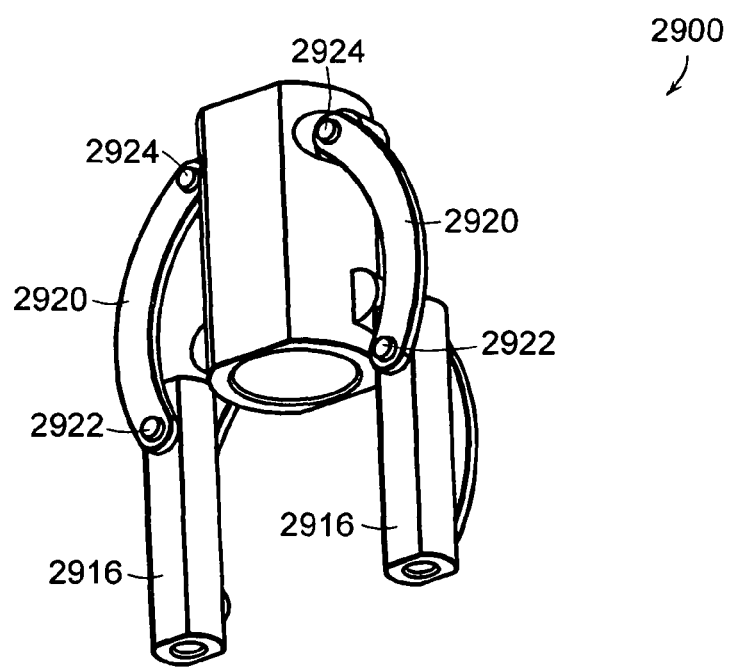

The present invention also includes a distraction instrument. FIG. 28 illustrates distraction instrument 2800 as one embodiment of the invention. Distraction instrument 2800 include a pair of first and second opposed distraction arms 2808 and 2810; wherein distraction arms 2808 and 2810 each define cannular pin sleeve 2812 sized to fit onto distraction pins 2814 anchored in vertebral bone 2816 such that a portion 2818 of each distraction pin distal to the vertebral bone 2816 is exposed after cannular pin sleeves 2812 are placed on distraction pins 2814; and distraction force transmitting member 2820 coupled to distraction arms 2808 and 2810.

In one embodiment, portion 2818 of each distraction pin that is exposed is at least about 50 percent of distraction pin 2814, by length. In another embodiment, portion 2818 of each distraction pin that is exposed is at least about 75 percent of distraction pin 2814, by length. As illustrated in FIG. 28, distraction force transmitting member 2820 is a dual threaded shaft. In other embodiments not illustrated, distraction force transmitting member 2820 can be a distraction force transmitting member such as a single threaded shaft, a rack and pinion mechanism, or a ratchet mechanism. In addition, distraction instrument 2800 can further include stabilizing member 2822 coupled to distraction arms 2808 and 2810. For example, distraction instrument 2800 can further include stabilizing member 2822 movably coupled to first distraction arm 2808 and fixably coupled to second distraction arm 2810. Stabilizing member 2822 can provide added stability to distraction instrument 2800.

The present invention also includes an intervertebral implant insertion guide. FIGS. 29A-29E illustrate intervertebral implant insertion guide 2900 according to one embodiment of the present invention. Intervertebral implant insertion guide 2900 includes cannular guide body 2910, defining cannular space 2912 shaped to receive intervertebral implant insertion instrument 2914; and two cannular pin sleeves 2916 sized to fit onto distraction pins 2814 anchored in vertebral bone 2816, wherein cannular pin sleeves 2916 are coupled to cannular guide body 2910. In one embodiment, cannular pin sleeves 2916 are parallel to each other.

As illustrated in FIGS. 29A-29E, cannular pin sleeves 2916 are coupled to the cannular guide body with movable linkages 2918. In one embodiment, at least one of cannular pin sleeves 2916 is connected to linking member 2920 via pivot 2922 and linking member 2920 is connected to cannular guide body 2910 via pivot 2924. Cannular pin sleeves 2916 can be movably coupled to cannular guide body 2910 such that cannular pin sleeves 2916 can be moved away from cannular guide body 2910 while maintaining orientation between cannular pin sleeves 2916 and cannular guide body 2910.

In one embodiment, the present invention also includes an additional method for inserting an implant into an intervertebral space. The method, illustrated in FIGS. 28 and 29A, includes: (a) placing distraction pins 2814 into adjacent vertebrae which abut the intervertebral space; (b) placing distraction instrument 2800 onto distraction pins 2814, such that a portion 2818 of each distraction pin distal to the vertebral bone 2816 remains exposed after placement of distraction instrument 2800 onto distraction pins 2814; (c) placing intervertebral implant insertion guide 2900 onto portions 2818 of the distraction pins that remained exposed after placement of distraction instrument 2800 onto the distraction pins 2814; and (d) inserting the implant into the intervertebral space using implant insertion instrument 2914, wherein implant insertion instrument 2914 is guided by intervertebral implant insertion guide 2900.

FIGS. 1-11, described supra, illustrate the placement of pins into adjacent vertebrae which abut the intervertebral space. In one embodiment, distraction pins are placed into a vertebra midline to the spine. In another embodiment, distraction pins are placed into a vertebra parallel to an endplate of the vertebra that abuts the intervertebral space. In a preferred embodiment, distraction pins are placed into a vertebra midline to the spine and parallel to an endplate of the vertebra that abuts the intervertebral space.

Placing distraction instrument 2800 onto distraction pins 2814, such that a portion 2818 of each distraction pin distal to the vertebral bone 2816 remains exposed after placement of distraction instrument 2800 onto distraction pins 2814 can include sliding cannular pin sleeves 2812 of distraction instrument 2800 onto distraction pins 2814. Placing intervertebral implant insertion guide 2900 onto portions 2818 of the distraction pins that remained exposed after placement of distraction instrument 2800 onto the distraction pins 2814 can include sliding cannular pin sleeves 2916 of intervertebral implant insertion guide 2900 onto distraction pins 2814. In one embodiment, the method further includes the step of inserting implant insertion instrument 2914 through cannular guide body 2910. For example, in one embodiment, implant insertion instrument 2914 is inserted through cannular guide body 2910 prior to placing intervertebral implant insertion guide 2900 onto distraction pins 2814.

The implant can be grasped using grasping mechanism 2926 of implant insertion instrument 2914. The implant can be grasped using implant insertion instrument 2914 prior to or following placing intervertebral implant insertion guide 2900 onto distraction pins 2814. Once the implant is correctly inserted into the intervertebral space, the implant can be released from grasping mechanism 2926. In one embodiment, the implant can be inserted into the intervertebral space midline to the spine. In other embodiments, the implant can be inserted into the intervertebral space parallel to the endplates of the vertebrae that abut the intervertebral space. In preferred embodiments, the implant can be inserted into the intervertebral space midline to the spine and parallel to the endplates of the vertebrae that abut the intervertebral space.

FIGS. 26A and 26B show implant 2510 positioned in the intervertebral space between adjacent vertebrae 2410 and 2412 following practice of this method.

In one embodiment, the method for inserting an implant into an intervertebral space typically further includes the step of preparing the intervertebral space for an implant prior to inserting the implant. Preparing the intervertebral space for an implant can include a partial or complete discectomy. In one embodiment, preparing the intervertebral space for an implant can include distraction of vertebrae, e.g., distraction of the adjacent vertebrae using distraction instrument 2800.

EQUIVALENTS

While this invention has been particularly shown and described with references to preferred embodiments thereof, it will be understood by those skilled in the art that various changes in form and details may be made therein without departing from the scope of the invention encompassed by the appended claims.

We claim:
1. A pin guide, comprising:
 a) a substantially planar support having first and second opposed surfaces, the support having a superior bore and an inferior bore extending between the first and second opposed surfaces;
 b) an intervertebral spacer formed on and projecting from the first surface of the support between the superior and inferior bores and configured to extend into an intervertebral space between adjacent superior and inferior vertebrae, the spacer having a superior surface extending from the first surface of the support inferior to the superior bore and an opposed, inferior surface extending from the first surface of the support superior to the inferior bore; and
 c) a plurality of elongate, parallel guide tubes extending from the second surface of the support, wherein the plurality of guide tubes comprise a superior guide tube defining a lumen aligned with the superior bore of the support and an inferior guide tube spaced apart from the superior guide tube and aligned with the inferior bore of the support, and wherein the parallel guide tubes are fixed relative to the intervertebral spacer and sized to align pins inserted into the guide tubes in a substantially parallel orientation in the superior and inferior vertebrae when the spacer is positioned within the intervertebral space such that the first surface of the support abuts the adjacent vertebrae and the superior surface of the spacer engages the superior vertebra and the inferior surface of the spacer engages the inferior vertebra.

2. The pin guide of claim 1 wherein a portion of the intervertebral spacer is removable.

3. The pin guide of claim 1 wherein the superior surface and the inferior surface skew toward one another.

4. The pin guide of claim 1 wherein at least one of the superior and inferior surfaces includes a textured surface.

5. The pin guide of claim 1 including two parallel guide tubes.

6. The pin guide of claim 1 wherein the parallel guide tubes project from the support in a direction opposite to the projecting intervertebral spacer.

7. The pin guide of claim 1 wherein each of the parallel guide tubes has a length greater than its diameter.

8. The pin guide of claim 1 wherein each of the parallel guide tubes has a length greater than a thread engagement length of a pin to be inserted into the guide tube.

9. The pin guide of claim 1 including an orientation marker.

10. The pin guide of claim 9 wherein the orientation marker is a marker hole defined by the pin guide.

11. The pin guide of claim 10 wherein the marker hole is cylindrical.

12. The pin guide of claim 1 constructed of a substantially radiopaque material.

13. The pin guide of claim 1 further including an instrument handle.

14. The pin guide of claim 13 wherein the instrument handle is a dovetailed projection.

15. A method for placing pins in adjacent vertebrae, comprising the steps of:
 a) positioning the intervertebral spacer of the pin guide of claim 1 between adjacent vertebrae; and
 b) placing pins in the adjacent vertebrae through at least two of the plurality of parallel guide tubes.

16. A pin guide, comprising:
 a support having first and second opposed surfaces, the support defining a superior bore and an inferior bore extending between the first and second opposed surfaces;
 an intervertebral spacer integral with and extending outward from the first surface of the support between the superior and inferior bores and configured to be positioned between adjacent superior and inferior vertebrae, the spacer having a superior surface extending from the first surface of the support inferior to the superior bore and an opposed, inferior surface extending from the first surface of the support superior to the inferior bore;
 at least two guide tubes spaced apart from one another and extending outward from the second surface of the support, each guide tube having a lumen extending therethrough aligned with one of the superior and inferior bores of the support, the guide tubes being configured to receive an instrument for guiding the instrument into the adjacent vertebrae when the spacer is positioned between adjacent vertebrae such that the first surface of the support abuts the adjacent vertebrae.

17. The pin guide of claim 16, further comprising a mating feature formed on the second surface of the support between the guide tubes.

18. The pin guide of claim 17, wherein the mating feature comprises a dovetailed projection.

19. The pin guide of claim 16, wherein the at least two guide tubes are parallel to one another.

20. The pin guide of claim 16, wherein the at least two guide tubes and the intervertebral spacer are parallel to one another.

21. The pin guide of claim 16, wherein the support includes at least one orientation marker formed thereon.

22. The pin guide of claim 1, wherein the parallel guide tubes have guide windows.

23. The pin guide of claim 16, wherein the at least two guide tubes have guide windows.

* * * * *